(12) United States Patent
Dubois et al.

(10) Patent No.: US 11,759,244 B2
(45) Date of Patent: *Sep. 19, 2023

(54) IMPLANT AND GUIDE

(71) Applicant: MATERIALISE NV, Leuven (BE)

(72) Inventors: Guillaume Dubois, Chatillon (FR); Patrick Goudot, Paris (FR); Thomas Schouman, Paris (FR)

(73) Assignee: MATERIALISE NV, Leuven (BE)

( * ) Notice: Subject to any disclaimer, the term of this patent is extended or adjusted under 35 U.S.C. 154(b) by 309 days.

This patent is subject to a terminal disclaimer.

(21) Appl. No.: 17/090,466

(22) Filed: Nov. 5, 2020

(65) Prior Publication Data

US 2021/0052309 A1   Feb. 25, 2021

Related U.S. Application Data

(63) Continuation of application No. 15/096,645, filed on Apr. 12, 2016, now Pat. No. 10,869,705, which is a
(Continued)

(30) Foreign Application Priority Data

Dec. 12, 2012   (FR) ...................... 12/03393

(51) Int. Cl.
*A61B 17/80* (2006.01)
*A61B 34/10* (2016.01)
(Continued)

(52) U.S. Cl.
CPC ........ *A61B 17/8061* (2013.01); *A61B 17/151* (2013.01); *A61B 17/1673* (2013.01); *A61B 17/176* (2013.01); *A61B 17/1728* (2013.01); *A61B 17/8071* (2013.01); *A61B 34/10* (2016.02); *A61F 2/2803* (2013.01);
(Continued)

(58) Field of Classification Search
CPC .... A61B 17/176; A61B 19/50; A61F 2/30942
See application file for complete search history.

(56) References Cited

U.S. PATENT DOCUMENTS 6,792,952 B2   9/2004   Mauro
8,764,441 B2   7/2014   Polley et al.
(Continued)

FOREIGN PATENT DOCUMENTS

CN   101637413 A   2/2010
CN   101637414 A   2/2010
(Continued)

OTHER PUBLICATIONS

Ciocca et al.: "CADCAM guided secondary mandibular reconstruction of a discontinuity defect after ablative cancer surgery" Journal of Cranio-Maxillo-Facial Surgery 40, e511-e515, 2012, Elsevier.
(Continued)

*Primary Examiner* — Andrew Yang
(74) *Attorney, Agent, or Firm* — EIP US LLP

(57) ABSTRACT

A method for configuring a surgical guide and an associated implant. The implant and surgical guide are for maxillofacial osteosynthesis. Three-dimensional models of the pre- and post-operative anatomy are used to define attachment points. These attachment points are used to determine a structure for the implant and surgical guide.

20 Claims, 20 Drawing Sheets

Related U.S. Application Data continuation of application No. 14/737,340, filed on Jun. 11, 2015, now Pat. No. 9,339,279, which is a continuation of application No. PCT/EP2013/076447, filed on Dec. 12, 2013.

(51) Int. Cl.

| | | |
|---|---|---|
| *A61B 17/15* | (2006.01) | |
| *A61B 17/16* | (2006.01) | |
| *A61F 2/28* | (2006.01) | |
| *A61B 17/17* | (2006.01) | |
| *G06T 17/00* | (2006.01) | |
| *A61B 17/68* | (2006.01) | |

(52) U.S. Cl.
CPC ............ *A61F 2/2875* (2013.01); *G06T 17/00* (2013.01); *A61B 2017/681* (2013.01); *A61B 2034/102* (2016.02); *A61F 2002/2882* (2013.01); *A61F 2002/2889* (2013.01)

(56) References Cited

U.S. PATENT DOCUMENTS

| | | |
|---|---|---|
| 2004/0070583 A1 | 4/2004 | Tsai et al. |
| 2004/0259051 A1 | 12/2004 | Branjnovic. |
| 2005/0038444 A1 | 2/2005 | Binder et al. |
| 2007/0118243 A1 | 5/2007 | Schroeder et al. |
| 2010/0036429 A1 | 2/2010 | Buck |
| 2010/0311006 A1 | 12/2010 | Lancieux et al. |
| 2011/0144647 A1 | 1/2011 | Brown et al. |
| 2011/0102549 A1 | 5/2011 | Takahashi |
| 2011/0213376 A1 | 9/2011 | Maxson et al. |
| 2011/0269100 A1 | 11/2011 | Furrer et al. |
| 2011/0301609 A1 | 12/2011 | Longepied |
| 2012/0029574 A1 | 2/2012 | Furrer et al. |
| 2012/0257841 A1 | 10/2012 | Liao |
| 2012/0310364 A1 | 12/2012 | Li et al. |
| 2015/0150684 A1 | 6/2015 | De Clerck |

FOREIGN PATENT DOCUMENTS

| | | |
|---|---|---|
| DE | 10 2006 043 204 A1 | 3/2008 |
| EP | 1726265 A1 | 11/2006 |
| EP | 2179701 A1 | 4/2010 |
| GB | 2324470 A | 10/1998 |
| JP | 2005-305150 A | 11/2005 |
| JP | 2006519636 A | 8/2006 |
| JP | 2007502171 A1 | 2/2007 |
| JP | 2012517842 A | 8/2012 |
| WO | 2004071309 A1 | 8/2004 |
| WO | 2006000063 A1 | 1/2006 |
| WO | 2008031562 A1 | 3/2008 |
| WO | 2010094857 A1 | 8/2010 |
| WO | 20110136775 A1 | 11/2011 |
| WO | 20110136898 A1 | 11/2011 |
| WO | 2011149106 A1 | 12/2011 |
| WO | 2013165558 A1 | 11/2013 |

OTHER PUBLICATIONS

Rosen et al: "Miniplate Fixation of Le Fort I Osteotomies", Plastic and Reconstructive Surgery, vol. 78, No. 6, Dec. 1986, pp. 748-754.
Eufinger et al: "Reconstruction of craniofacial bone defects with individual alloplastic implants based on CAD/CAM-manipulated CT-data", Journal of Cranio Maxillo-Facial Surgery, vol. 23, 1995, pp. 175-181.
Wehmoller et al: "CAD by processing of computed tomography data and CAM of individually designed prostheses", Int. J. Oral Maxillofac. Surg. vol. 24, 1995, pp. 90-97.
Peckitt, N.S.: "Stereoscopic lithography: customized titanium implants in orofacial reconstruction", British Journal of Oral and Maxillofacial Surgery, vol. 37, 1999, pp. 353-369.
Mehra, Pushkar: "Stability of maxillary advancement using rigid fixation and porous-block hydroxyapatite grafting: Cleft palate versus non-cleft patients" Int J Adult Orthod Orthognath Surg vol. 16, No. 3, 2001, pp. 193-199.
Amin et al: "New techniques in facial trauma reconstruction", Trauma 2002, vol. 4, pp. 65-77.
Muller et al.: "The Application of Rapid Prototyping Techniques in Cranial Reconstruction and Preoperative Planning in Neurosurgery", The Journal of Craniofacial Surgery / vol. 14, No. 6 Nov. 2003, pp. 899-914.
Bill et al: "Rechnergestützte Modellbauverfahren zur Planung ausgedehnter Rekonstruktionseingriffe im Schädelbereich" Mund Kiefer GesichtsChir 2004 •8 :135-153.
Singare et al: "Design and fabrication of custom mandible titanium tray based on rapid prototyping", IPEM, Jun. 2004, pp. 1350-4533.
AO Development News, No. 1, 2004.
Gibson, I.: Advanced Manufacturing Technology for Medical Applications: Reverse Engineering, Software Conversion and Rapid Prototyping, 2005 John Wiley & Sons, Ltd.
Sandor et al.: "Distraction Osteogenesis of the Midface", Oral Maxillofacial Surg Clin N Am 17 (2005) pp. 485-501.
Singare et al: "Customized design and manufacturing of chin implant based on rapid prototyping", Case Study Rapid Prototyping Journal, 11/2 (2005) pp. 113-118.
Xia et al.: "Three-Dimensional Computer-Aided Surgical Simulation for Maxillofacial Surgery", Atlas Oral Maxillofacial Surg Clin N Am 13 (2005) pp. 25-39.
Hiew et al.: "Optimal Occlusion of Teeth", ICARCV 2006.
Metzger et al.: "Anatomical 3-dimensional Pre-bent Titanium Implant for Orbital Floor Fractures", Ophthalmology 2006; 113, 2006, pp. 1863-1868.
Caloss, et al.: "Three-Dimensional Imaging for Virtual Assessment and Treatment Simulation in Orthognathic Surgery", Oral Maxillofacial Surg Clin N Am 19 (2007) pp. 287-309.
Metzger et al: "Semiautomatic Procedure for Individual Preforming of Titanium Meshes for Orbital Fractures", Plastic and Reconstructive Surgery, Mar. 2007, pp. 969-976.
Toro et al.: "Feasibility of preoperative planning using anatomical facsimile models for mandibular reconstruction" Head & Face Medicine 2007, 3:5.
Singare et al.: "Individually Prefabricated Prosthesis for Maxilla Reconstruction", Journal of Prosthodontics 17 (2007) 135-140.
Wang et al.: "Biomechanical Evaluation of Le Fort I Maxillary Fracture Plating Techniques" J Oral Maxillofac Surg 65:1109-1116, 2007.
Metzger et al.: "Manufacturing splints for orthognathic surgery using a three-dimensional printer", Oral Surg Oral Med Oral Pathol Oral Radiol Endod 2008;105:e1-e7.
Bibb et al.: "Rapid manufacture of custom-fitting surgical guides", Rapid Prototyping Journal, 15/5 (2009) 346-354.
Grecchi et al: "Computer planned implant-orthognathic rehabilitation: a case of one step surgical procedure with implants insertion, Le Fort I advancement, grafting and immediate loading", Journal of Osseointegration • Dec. 2009;3(1): pp. 95-103.
Grecchi et al: "One-Step Oral Rehabilitation by Means of Implants' Insertion, Le Fort I, Grafts, and Immediate Loading", The Journal of Craniofacial Surgery & vol. 20, No. 6, Nov. 2009 pp. 2205-2210.
Hirsch et al.: "Use of Computer-Aided Design and Computer-Aided Manufacturing to Produce Orthognathically Ideal Surgical Outcomes: A Paradigm Shift in Head and Neck Reconstruction", J Oral Maxillofac Surg 67:2115-2122, 2009.
Schramm et al.: "Computer-assisted therapy in orbital and mid-facial reconstructions", Int J Med Robotics Comput Assist Surg 2009; 5: 111-124.
Singare et al.: "Rapid prototyping assisted surgery planning and custom implant design", Rapid Prototyping Journal 15/1 (2009) 19-23.
MatrixOrthognatic Plating System. Specialized implants and instruments for orthognathic surgery, Technique guide, 2009.
Tucker, Scott: "Orthognathic Surgical Simulation of Class III Patients Using 3-D Cone Beam CT Images", Chapel Hill, 2009.

(56) References Cited

OTHER PUBLICATIONS

Bell, Ryan: "Computer Planning and Intraoperative Navigation in Cranio-Maxillofacial Surgery", Oral Maxillofacial Surg Clin N Am 22 (2010) 135-156.
Hardt et al.: Craniofacial Trauma, 2010.
Edwards, Sean: "Computer-Assisted Craniomaxillofacial Surgery", Oral Maxillofacial Surg Clin N Am 22 (2010) 117-134.
Katikaneni et al.: "Computer-Assisted Virtual Planning in Maxillofacial Reconstruction Using Microvascular Free Fibula Flaps", AAOMS, 2010, e26-27.
Lethaus et al: "Reconstruction of a maxillary defect with a fibula graft and titanium mesh using CAD/CAM techniques", Head & Face Medicine 2010, 6:16.
Olszewski et al. "Innovative procedure for computer-assisted genioplasty: three-dimensional cephalometry, rapid-prototyping model and surgical splint" Int'l Journal of Oral and Maxillofacial Surgery 2010; 39: 721-724; Mar. 18, 2010.
Popat et al.: New developments in: three-dimensional planning for orthognathic surgery, Journal of Orthodontics, vol. 37, 2010, 62-71.
McCormick, et al.: "Virtual Model Surgery for Efficient Planning and Surgical Performance", J Oral Maxillofac Surg 69:638-644, 2011.
Japanese Office Action dated Jun. 25, 2019 for JP Application No. JP2018-138585.
Hirsch DL, Garfein ES, Christensen AM, Weimer KA, Saddeh PB, Levine JP. "Use of computer-aided design and computer-aided manufacturing to produce orthognathically ideal surgical outcomes: a paradigm shift in head and neck reconstruction" J. Oral Maxillofac. Surg. Oct. 2009; 67(10):2115-22.
Robiony M, Salvo I, Costa F, Zerman N, Bazzocchi M, Toso F, et al. "Virtual reality surgical planning for maxillofacial distraction osteogenesis: the role of reverse engineering rapid prototyping and cooperative work". J. Oral Maxillofac. Surg. Jun. 2007; 65(6):1198-208.
Scolozzi P, Schouman T. "Interventional multimodal hybrid unit: from pre-operative planning to immediate post-operative control". Rev Stomatol Chir Maxillofac. Apr. 2012; 113(2):115-23.
Cevidanes LHC, Tucker S, Styner M, Kim H, Chapuis J, Reyes M, et al. "Three-dimensional surgical simulation". Am J Orthod Dentofacial Orthop. Sep. 2010; 138(3):361-71.
Bai S, Bo B, Bi Y, Wang B, Zhao J, Liu Y, et al. "CAD/CAM surface templates as an alternative to the intermediate wafer in orthognathic surgery". Oral Surgery, Oral Medicine, Oral Pathology, Oral Radiology, and Endodontology. Nov. 2010; 110(5):e1-e7.
Bai S, Shang H, Liu Y, Zhao J, Zhao Y. "Computer-aided design and computer-aided manufacturing locating guides accompanied with prebent titanium plates in orthognathic surgery". J. Oral Maxillofac. Surg. Oct. 2012; 70(10):2419-26.
Roser SM et al. "The accuracy of virtual surgical planning in free fibula mandibular reconstruction: comparison of planned and final results". J Oral Maxillofac Surg. Nov. 2010; 68(11):2824-32. Epub Sep. 9, 2010.
French Search Report dated Aug. 26, 2013 for French Application No. FR 1203393.

IMPLANT AND GUIDE

CROSS-REFERENCE TO RELATED APPLICATIONS

This application is a continuation of U.S. application Ser. No. 15/096,645, filed on Apr. 12, 2016, which is a continuation of U.S. application Ser. No. 14/737,340, filed on Jun. 11, 2015, which is a continuation under 35 U.S.C. § 120 of International Application Number PCT/EP2013/076447, filed Dec. 12, 2013 (and published on Jun. 19, 2014 in the English language as WO2014/090964), which claims priority to French patent application number 12/03393, filed Dec. 12, 2012. Each of the above-referenced patent applications is hereby incorporated by reference.

BACKGROUND OF THE INVENTION

Field of the Invention

The present invention relates to a technique for repositioning bone portions for bone surgery, in particular for facial surgery, the technique being based on the use of customized implants and guides.

Description of the Related Technology

Some surgical interventions are intended to correct bone deformations, occurrences of disharmony or proportional defects of the face, or post-traumatic after-effects. These interventions use actions for repositioning, in an ideal location, some fragments of bone which have been separated from a base portion beforehand by a surgeon.

Such surgical interventions therefore comprise an osteotomy which is carried out in order to release one or more badly-positioned bone segments; for example, to move this or these bone segment(s), that is to say, to move it/them by way of translation and/or by rotation in order to be able to reposition it/them at their ideal location after this movement.

When all bone segments occupy a new ideal position, the surgeon fixes the bone segments to other adjacent bone portions of the patient using for one or more implants. These may comprise perforated implants, which may have different geometries, for example, in the form of I-shaped, L-shaped, T-shaped, X-shaped, H-shaped or Z-shaped plates, or more complex geometries. The implants are fixed to all the portions of bone to be joined in their correct relative positions using osteosynthesis screws which extend through their perforations.

It is then, in this way, possible to seek to restore the symmetry of the face or normal anthropometric relationships.

U.S. Pat. Nos. 5,690,631 and 6,221,075 describe such implants in the form of plates or trellises which are capable of allowing at least two bone portions to be joined and fixed to each other.

Amongst the various forms of surgery which affect the facial skeleton, it is possible to mention:
- orthognathic surgery, the objective of which is to reposition dental bridges in relative comfortable positions, ensuring good engagement of the teeth; such an intervention involves a maxillary osteotomy if it is necessary to move the upper dental bridge, or a mandibular osteotomy if it is necessary to move the lower dental bridge, or a bi-maxillary osteotomy if it is advantageous to move segments of bone on the two jaws in order to also re-establish the normal proportions of a face,
- genioplasty involving an operation on the chin of a patient for aesthetic matters (in order to correct an excessively protruding chin or in contrast a receding chin) or for functional matters, for example, allowing a patient to be able to move his lips into contact with each other without effort,
- the correction of post-traumatic after-effects, for example, with regard to the zygomatic bone, following accidental impacts.

A technique for producing a made-to-measure preformed implant is described in an International Patent Application published on 3 Nov. 2011 under the number WO 2011/136898. The technique therein comprises the production of a made-to-measure guide which is also pre-shaped and which serves to guide the drilling of some holes for the osteosynthesis screws and which also serves to guide an osteotomy.

A disadvantage of the aforementioned prior technique is that it is dependent on the quality of the osteotomy, or the resection operation, carried out by the surgeon.

An object of certain embodiments of the invention disclosed herein is to overcome such a disadvantage. For example, it is desired to have excellent connection of the first portion of the bone and the second portion of the bone, even if the osteotomy and/or the resection were to be imperfect, imprecise and even approximate.

DETAILED DESCRIPTION OF CERTAIN INVENTIVE EMBODIMENTS

Figure 2:
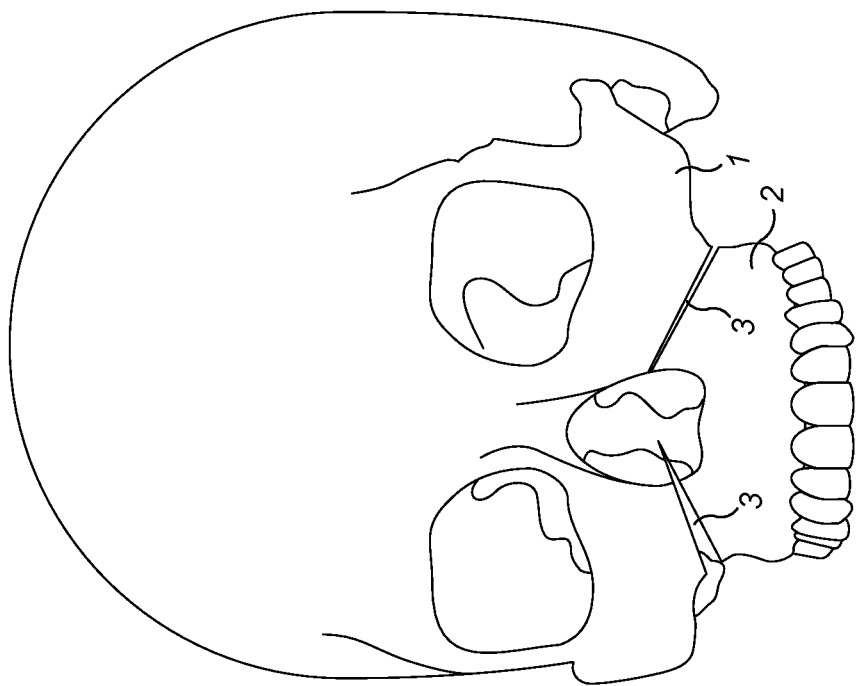
FIGS. 1 to 9 illustrate a method according to an example that allows a development of a made-to-measure implant and drilling guide.

Techniques used in certain examples described herein involve producing a pre-operative model and a modified model of a complete bone in three dimensions. In certain cases these models are digitalized and used to produce an implant and/or drilling guide. The implant and/or drilling guide may be bespoke, i.e. made-to-measure or customized for a patient.

In cases, pre-operative planning of the repositioning operations to be carried out for various bone fragments or portions is desirable in order to define an ideal position of the bone fragments or portions.

The pre-operative planning generally uses radiography studies or tomodensimetric scanner sections. These imaging data are then processed on a computer using a specific application to generate a three-dimensional reconstruction of the images. For example, this stage may comprise accessing data indicative of a pre-operative maxillofacial anatomy of a patient and generating a three-dimensional model of said anatomy using said data.

When the planning is complete, a pre-operative model of a bone structure, such as a skull or a portion thereof, in three dimensions is produced. This constitutes the pre-operative shape of the bone. This shape is then modified to produce a modified model corresponding to the planned post-operative shape of the bone, in three dimensions.

Amongst the means to achieve this, a surgeon can, optionally in collaboration with an engineer, use a system of surgical navigation by means of which it will be possible for him to define on the modified model the various planes of section which will then allow the bone fragments to be moved, separated virtually from their base owing to the osteotomy, in order to move them in one or more directions to be determined in order to be able to reposition them in the correct location.

In this manner, an osteotomy is simulated on the three-dimensional model of the pre-operative maxillofacial anatomy. In one case, said simulated osteotomy defines at least one cut that results in one or more bone portions that are separated from other one or more bone portions. In certain cases, said at least one cut results in an absence of any bone coupling the bone portions together, i.e. the cut is a complete cut that completely separates at least one bone portion from one or more other bone portions. The cut may thus result in an absence of a continuous bone coupling between bone portions.

After this virtual osteotomy, the second step involves carrying out, still in a virtual manner, the ideal repositioning of various bone segments.

The repositioning or arranging of one or more bone portions in relation to one or more other bone portions enables a modified three-dimensional model to be generated. This model is indicative of a desired post-operative orientation of the bone portions.

To this end, the surgeon generally uses criteria of symmetry or cephalometry.

The repositioning operations carried out are transformations which combine movements in translation and/or in rotation. In one case, the arrangement may comprise at least one or more of a translation of the one or more bone portion in relation to one or more other bone portions and a rotation of the one or more bone portions about an axis that is orientated at a non-zero angle to an osteotomy plane, e.g. at least one plane of a virtual osteotomy cut within an original pre-operative model. In more complex operations the osteotomy may be according to a complex shape that resides in multiple planes. In certain cases, in the surgical procedure that follows the virtual osteotomy, the cut may be partial, with a complete separation being achieved by one or more fractures applied by a surgeon.

It is during this second step that the surgeon also defines any bone zones to be resected in the event that some bone fragments could overlap each other when they are moved together, at least as the surgeon sees them on the computer screen.

A technician or an engineer, possibly in close collaboration with the surgeon, may thus physically design during a third step one or more implants. In one case, they may also be responsible for the virtual osteotomy and/or repositioning, and/or this may be performed in association with a medically trained professional. Following the manufacture of the one or more implants according to the design, a surgeon is able to fix said implants to the different bone fragments, after having carried out an actual, as opposed to virtual, osteotomy operation. The operation may also optionally include a resection operation. The operation maintains the bone fragments in the correct position, which are secured by way of the one or more implants. The implants may remain for the time necessary for good reconstruction and good bone consolidation.

Certain examples are set out in the following description together with the appended drawings. It should be noted that these drawings are intended only to illustrate the text of the description and as such are not limiting.

In certain examples, there is a method which involves producing in a made-to-measure state one or more of (a) a pre-shaped implant and (b) a pre-shaped guide which is used to guide the drilling of holes for all the screws required for the future fixing of the implant to the portions of bone to be fixedly joined together after a maxillofacial osteotomy operation. The pre-shaped guide may also, in certain cases, comprise an osteotomy template to guide the osteotomy. One example method will be described with reference to FIGS. 1 to 9.

The orthognathic surgery, the different preparation phases of which are illustrated by way of first example in FIGS. 1 to 9, is intended to repair an occurrence of asymmetry, the intervention involving in this instance a maxillar osteotomy. In certain case, this could be combined with chin surgery of the type illustrated in FIGS. 20 to 25.

Figure 1:
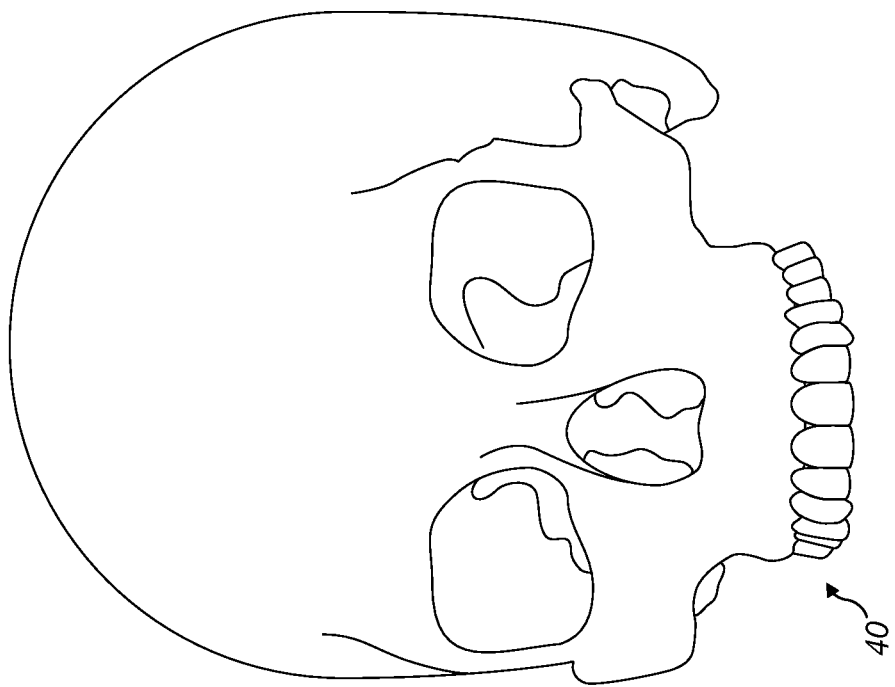

As described above, a technician, most often in collaboration with a surgeon, using a computer, first produces a pre-operative model 40 of the bone, in three dimensions, which constitutes the pre-operative shape of the bone (FIG. 1). For example, in this case the pre-operative model is of a portion of a skull. The model of the bone may be a model of a complete portion of bone involved in a repositioning operation.

Figure 3:
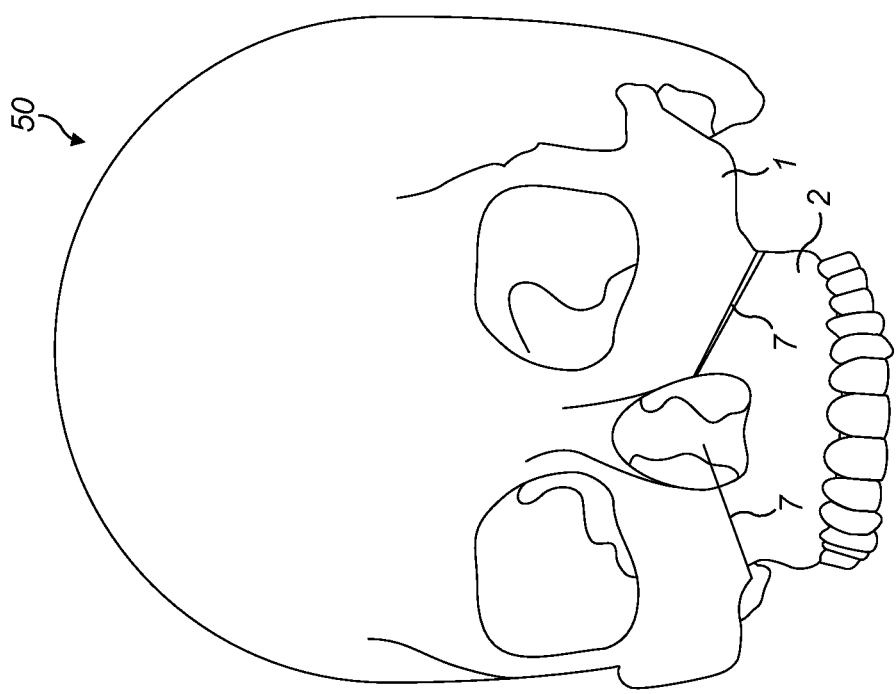

Using dedicated planning software, for example, the software marketed by the Belgian company Materialise under the name Mimics, a user, typically a medically trained professional such as a surgeon, optionally assisted by a technician, modifies the pre-operative model by carrying out a virtual osteotomy 3 (FIG. 2), following which he arrives at a modified model 50 which gives the ideal result which is desired by the surgical intervention and consequently corresponds to a planned shape of the bone (FIG. 3). For example, this may be a desired post-operative orientation of the first and second bone portions. The model is modified at a pre-operative stage. In FIG. 3 the ideal result is an arrangement of an upper jaw portion (2) with respect to the skull (1). This for example may reflect a desired alignment of the upper and lower jaws, an alignment via trauma or fracture of the bone, and/or an alignment to correct a deformity.

As has been said above, at the same time as he virtually carries out his osteotomy, the user, such as a surgeon, may envisage carrying out one or more resection operations in the event of interference between some bone fragments, in order to achieve perfect positioning of the separated portion of the bone 2 in the portion 1 of the base bone.

In the present description, the portion 1 of the base bone will be referred to as "first portion of the bone" and the separated portion 2 (or the separated portions) will be referred to as "second portion of the bone". However, as described elsewhere in this specification, the method may apply to multiple bone portions, such that one or more of the first and second bone portions may comprise a plurality of bone fragments, and/or relate to other bone portions to be repositioned.

After ideal repositioning of the second portion 2 of the bone on the first portion 1 in the virtual three-dimensional space of the modified model, the user defines the future fixing locations for the two portions of bone using one or more implants. In this case the fixing locations are associated with the axes of the osteosynthesis screws which ensure perfect fixing of the one or more implants on the portions of bone to be fixedly retained in their desired correct relative position by the user.

Figure 4:
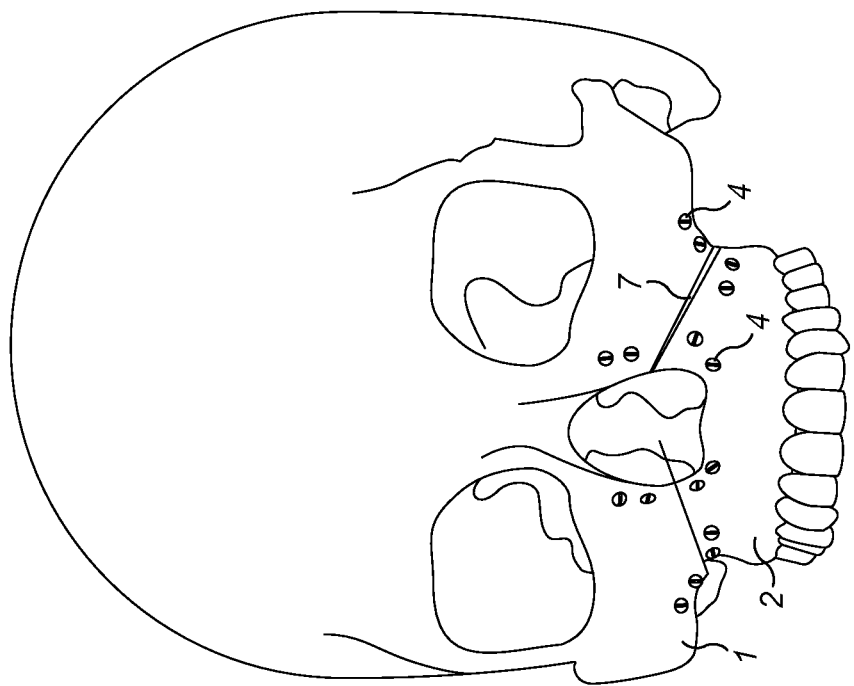

Such fixing locations 4 (for example, eight in number in the first portion 1 of the bone and also eight in the second portion 2 of the bone) are provided in sufficient numbers to ensure anchoring of the second portion 2 of the bone on the first portion 1 (FIG. 4).

In the present examples, the future fixing locations, referred to here as attachment points, comprise a first plurality of attachment points for the implant on the first bone portion and a second plurality of attachment points for the implant on the second bone portion. For example, in FIG. 4 there are eight points on each bone portion.

As described above and shown in FIG. 4, the first and second plurality of attachment points are defined on the modified three-dimensional model based on at least one location of one or more anatomical features of a patient. For example, fixing locations or attachment points may be defined to avoid numerous anatomical obstacles such as at least one or more of the following: teeth roots, nerves and/or blood vessels inside the bone portions. Likewise, some bone parts are very thin, e.g. this is especially true of maxillary regions, which leading to difficulties to obtain stable osteosynthesis. By defining the fixing locations, screws can be individually placed in the most favorable locations to ensure successful repositioning without complication; for example, with greatly reduced risk of damaging any important anatomical structure and with screw placement in regions with the best bone quality.

In practice, as shown in FIG. 4, this results in, when compared with a comparative example, at least a spacing distance between a first set of adjacent attachment points being different from a spacing distance between a second set of adjacent attachment points. In this case the first and second sets of adjacent attachment points comprise either: two sets of attachment points with each set comprising adjacent attachment points on the same bone portion; or two sets of attachment points with each set comprising a first attachment point on the first bone portion and a second, adjacent attachment point on the second bone portion. This means that the attachment points are typically not defined in a standard square or rectangular relationship: individual placement leads to variation in the relative spacing between attachment points. Not all fixing locations need to be individually placed, but at least one is placed so as to avoid high-risk areas of anatomy.

According to certain examples described herein, following the defining of the fixing locations or attachment points, a monolithic three-dimensional structure is defined for the implant. This structure couples the first and second plurality of attachment points in the modified three-dimensional model. The defined structure has a shape that varies in each of three dimensions to arrange or align the second bone portion relative to the first bone portion in accordance with the desired post-operative orientation. In this case, each of at least one of the attachment points correspond to an aperture for a bone fixation device in said structure for the implant, e.g. each fixing location may correspond to a hole where a bone screw fixes the implant to a bone portion.

For example, the user may subsequently draw the implant 5 which can be seen in FIG. 9. The sixteen osteosynthesis screws which ensure that the implant is fixed in the first and second portions of the bone are designated by the locations 6. These screws correspond precisely to the fixing locations or attachment points 4, which can be seen in FIG. 4.

In the above example, the fixing locations or attachment points are defined prior to the structure of the implant; in effect, the structure of the implant is designed around the placement of the fixing locations. For example, in FIG. 9, the implant comprises portions in the form of members that couple certain adjacent apertures for the attachment screws.

The implant 5 is thus arranged at a pre-operative stage so as to correspond to the planned post-operative shape of the desired anatomy. As well as being customized in the form of customized couplings between individually placed screw apertures, the implant 5 is also pre-shaped in such a manner that the congruence of surfaces of intrados thereof allows unique and precise positioning on the two portions of bone to be joined at the end of the surgical operation. In other words the implant has a shape that varies in three dimensions to arrange the second bone portion relative to the first bone portion in accordance with the desired post-operative orientation and the implant has a shape that matches the anatomy of both the first and second bone portions. The term intrados, meaning the underside of an arch, is used to refer to the curvature of the implant, in particular in the present example, an inner curvature that mates with an outer curvature of the bone portions. Such curvature is bespoke for each patient, the example the inner surface of the implant 5 may vary in a non-uniform manner with multiple undulations that reflect the anatomy of the patient. In this case, a first portion of the implant structure has a three dimensional shape, including a defined inner surface or plane, that matches an outer surface or plane as defined by the anatomy of the first portion of bone, i.e. the upper skull. A second portion of the implant structure then has a three dimensional shape, including a defined inner surface or plane, that matches an outer surface or plane as defined by the anatomy of the second portion of bone, i.e. the upper jaw portion that is to be realigned with respect to the upper skull.

The implant 5 extends at both sides of one or more osteotomy lines 7. The one or more osteotomy lines 7 each define a cut containing the line which separates the two portions of bone 1, 2. The structure of the implant 5 comprises, with respect to the second portion 2 of the bone, through-holes for screws that correspond to drilling guiding holes or attachment points for screws as defined on the modified model.

Figure 9:
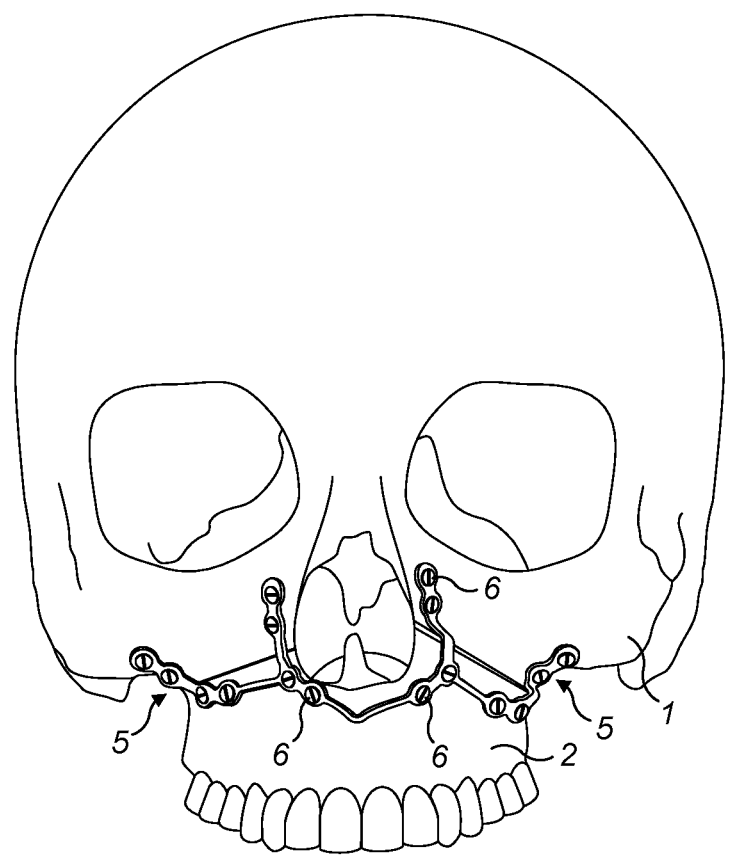

The implant 5 may be manufactured or produced based on the defined structure, e.g. based on a three-dimensional model such as that shown in FIG. 9. The implant may be manufactured by additive manufacturing, for example it may be printed in three dimensions or selective laser sintering.

In contrast to comparative examples, the through-holes of the implant 5, for the passage of the screws which are intended to allow the implant to be fixed to the first portion of the bone, are not provided in a completely arbitrary, unplanned manner. Instead in certain examples described herein, such holes, with respect to the first portion 1 of the bone, are provided so as to correspond to the attachment points or fixing locations as defined on the modified model.

In the presently described example, using a computer application, a user, e.g. a technician in certain cases assisted by a surgeon, carries out a reverse transformation of the ideal repositioning which he has carried out. In other words he returns to the pre-operative model of the bone which constitutes the pre-operative shape of the bone. In this case the first and second plurality of attachment points are mapped to corresponding locations on the three-dimensional model of the pre-operative maxillofacial anatomy.

For example, on the original model of the pre-operative maxillofacial anatomy (FIG. 5), the user defines, for example, using virtual models of drill bushes or bits 8, the positions of the bores. In this case these positions are derived from, i.e. correspond to, the fixing locations 4 planned previously with respect to the modified model (FIG. 4). In the example shown in FIGS. 1 to 9, the fixing locations 4 on the first portion 1 may be mapped directly between the modified and unmodified models: the location of the first portion of bone 1 in three dimensional space does not change between the modified and unmodified models. In the same example the fixing locations 4 on the second portion 2 are mapped based on their relative positioning with respect to the second portion 2. In this latter case, the location, position and/or orientation of the second portion changes with respect to the first portion between the modified and unmodified models as a result of the virtual osteotomy. Hence, the fixing locations 4 may be mapped by applying a function that is inverse to a function defining the translation and/or rotation that resulted from the virtual osteotomy. In both cases the mapping may be achieved by applying a function to a three dimensional co-ordinate or model component.

Following the mapping stage, a monolithic three-dimensional structure for the surgical guide is determined that couples the corresponding locations in the three-dimensional model of the pre-operative maxillofacial anatomy. For example, in one case a user may "draw" or otherwise define within the virtual model, the surgical guide which corresponds to the pre-operative shape of the bone and which comprises the drilling guiding holes for the fixing screws. In a preferred case, the position of the osteotomy or the osteotomies to be carried out may also be defined by way of the surgical guide structure. An exemplary surgical guide as defined as a three-dimensional model is shown in FIG. 6.

Figure 6:
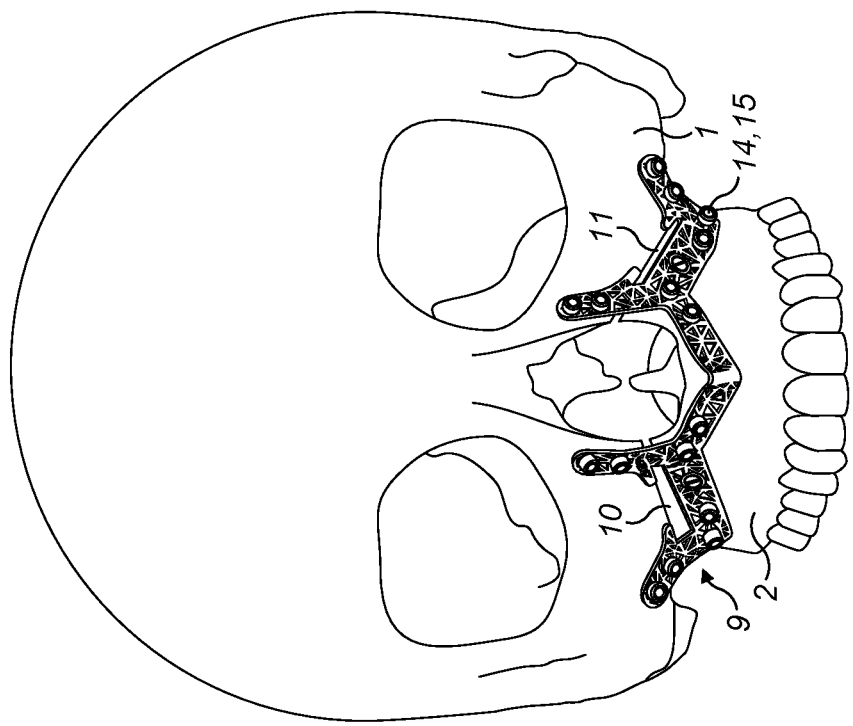
Figure 5:
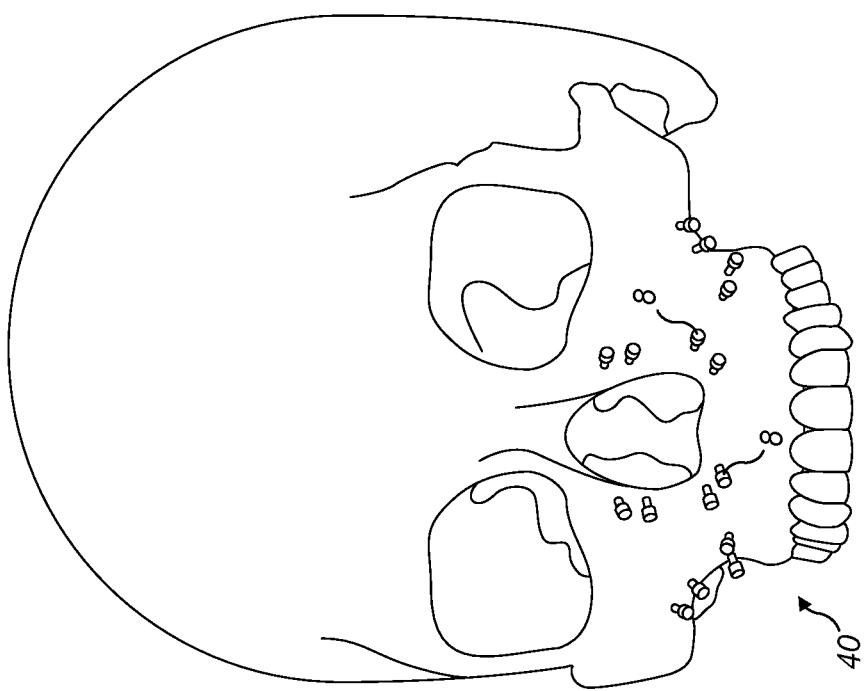

The drilling guide 9 which is defined in this manner and which can be seen in FIG. 6 consequently comprises:

drilling guiding holes for the screws corresponding, in terms of the second portion 2 of the bone which must be separated, to the drilling guiding holes for the screws of the modified model provided with respect to the second portion, two notches 10 and 11 which correspond to the templates of the future osteotomies.

The notches may comprise elongate openings with the three dimensional guide structure that are arranged to allow a passage of a cutting tool, such as a bone saw, to perform the respective one or more osteotomies.

As was the case for the implant, the drilling guide is configured so that there is excellent correspondence between the surfaces of the intrados thereof and the bone support or anatomy of the patient. In this manner there exists only one possible position for such a guide with respect to the anatomy of the patient; e.g. the guide may only sit flush with the bone portions of the patient in one unique spatial position or configuration. In this case, if the guide is placed in an incorrect orientation with respect to the bone portions the guide, it will not sit properly, i.e. it will be in an unstable configuration, such that movements to work the guide into a correct configuration result in a stable mating of an inner surface defined by the guide and an outer surface defined by the bone portions. This enables a simpler and more precise surgical operation to be carried out at a later stage.

The guide 9 according to the present example comprises drilling guiding holes for the screws for the first portion of the bone (in additional to those for the second portion of bone), the precise position of these holes having been defined during the operation which can be seen in FIG. 4.

Figure 7:
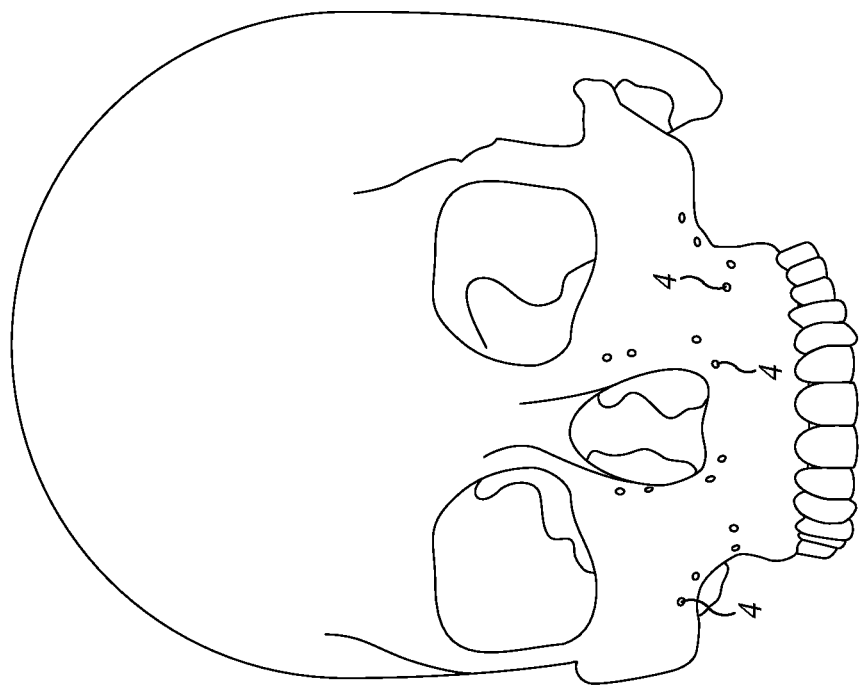

FIG. 7 shows the pre-operative or unmodified model in which a plurality of bores have been defined in the first and second bone portions within the model for the passage of the screws which are intended to allow the future fixing of the implant 5. In this case the relative spatial arrangement of the bores is different from the relative spatial arrangement of the fixing locations 4 seen in FIG. 4 because, at the stage illustrated in FIG. 7, the virtual osteotomy and repositioning operations have not yet been carried out. These bores represent the holes that are to be drilled for previously-defined fixing locations or attachment points.

Figure 8:
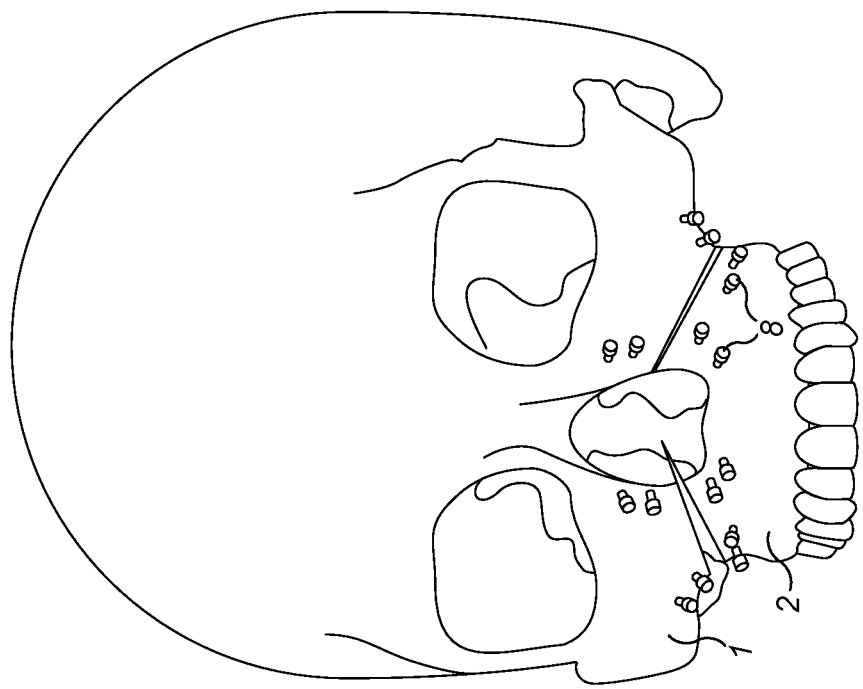
Figure 10A:
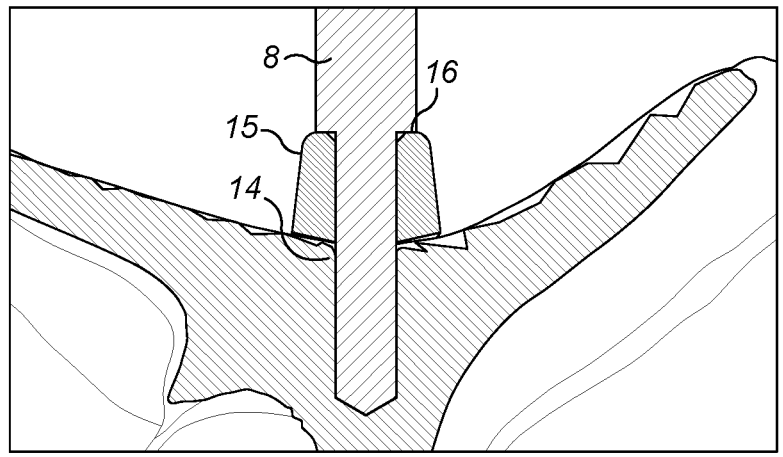
FIG. 10a illustrates a longitudinal section of a drill bush associated with a drilling guiding hole of an example drilling guide, the drill bush being associated with a stop bit.
Figure 10B:
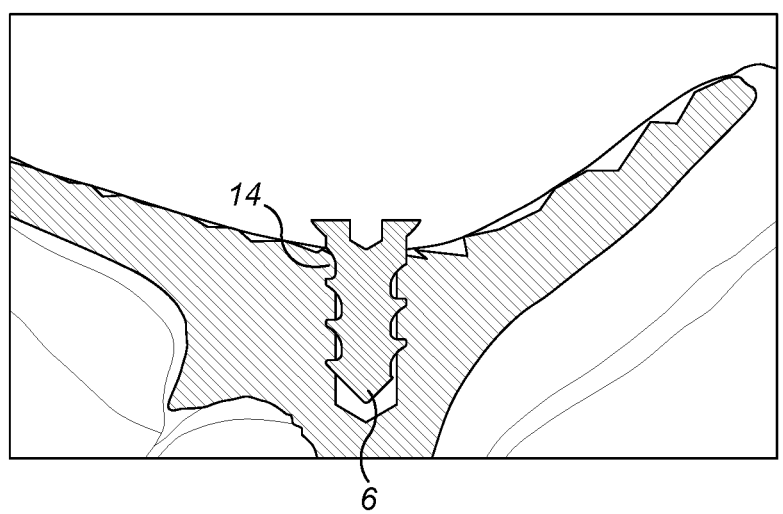
FIG. 10b shows an osteotomy fixing device in situ within a drilled bore.

FIG. 8 shows the different locations of a plurality of drill bits 8 (or at least an end portion of a drill bit) in the first portion 1 of the bone and second portion 2 of the bone after osteotomy, but before repositioning. In this case the drill bits 8 are modelled within the virtual three-dimensional model. Further detail is shown in FIGS. 10a and 10b. Modelling the drill bits 8 may aid in defining the height of one or more drill bushes 15 as described later below.

Finally, FIG. 9 shows a simulation of the two portions of the bone joined after an osteotomy and repositioning operations. Once the implant 5 and guide 9 have been determined, i.e. designed, within a virtual three-dimensional space they may be manufactured for use in the osteotomy and repositioning operations. FIG. 9 is thus illustrative of the use of an implant 5 following surgical operations. The joining of the two portions of bone is securely held using the implant 5. The implant may remain indefinitely or as long as a medical professional deems it necessary to allow the two portions of bone to be fixed and consolidated. For example, in a case similar to FIG. 9 bone may grow to join both the first and second portions in the configuration set by the implant 5.

FIGS. 1 to 9 illustrate the different preparation phases in the customized production of a pre-shaped implant 5 and a pre-shaped guide 9. Following this, the orthognathic surgical operation in which a manufactured implant and guide may be used will now be described with reference to FIGS. 11 to 19.

Figure 11:
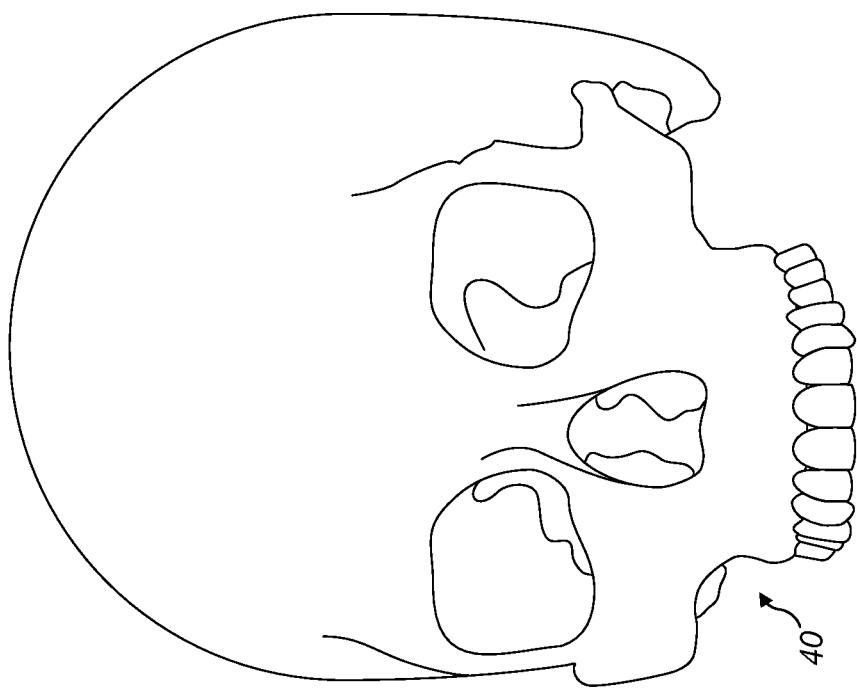

The facial skeleton 40 to be repaired is illustrated in FIG. 11 which mirrors the virtual model of FIG. 1.

A surgeon places the guide 9 which is produced in a made-to-measure state on the face of the patient. In one case, e.g. if the operation is to be simple and brief, the guide 9 may be held by hand in the position shown in FIG. 12. In another case, e.g. if the operation is to be relatively long, the guide may be temporarily fixed using one or more osteotomy screws, for example on one or more sides of the osteotomy or cutting template 3, as shown in FIG. 13. In certain cases at least one of said one or more apertures for attaching the surgical guide 9 is coincident with a defined osteotomy cut.

Figure 12:
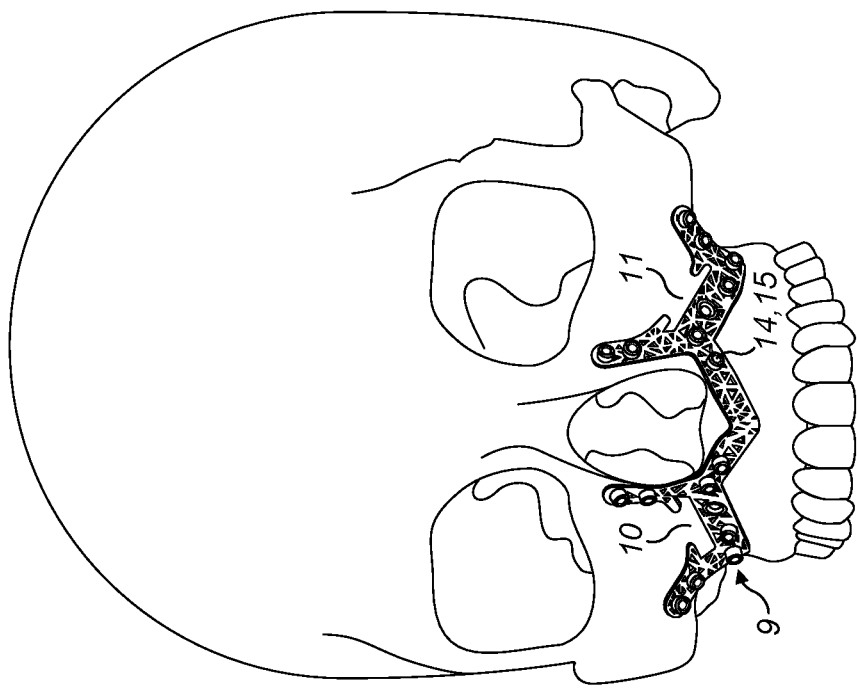
FIGS. 11 to 19 illustrate different steps of an orthognathic surgical operation that can be carried out using the drilling guide and the implant obtained by carrying out the method illustrated in FIGS. 1 to 9.
Figure 14:
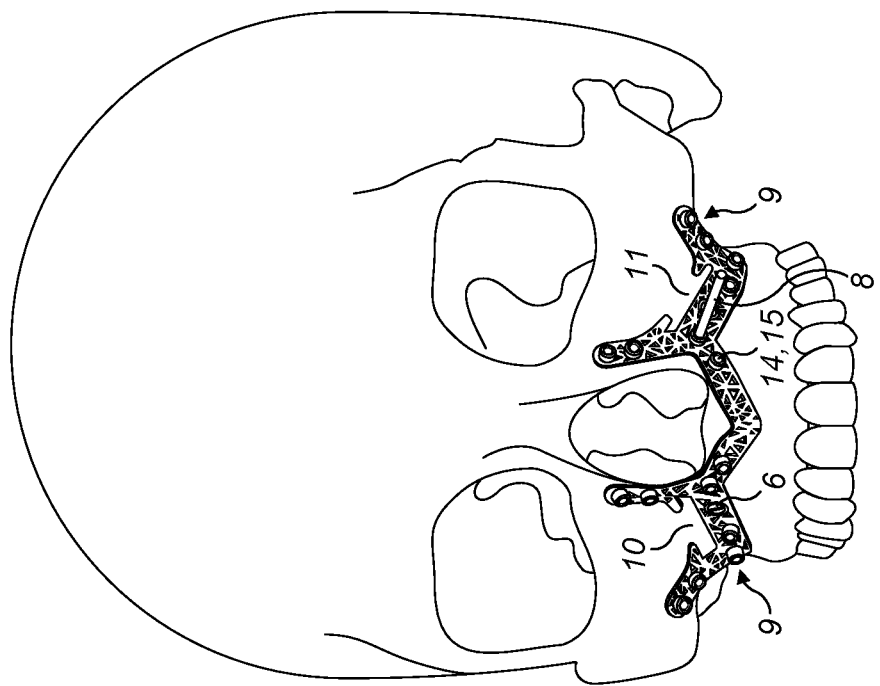
Figure 13:
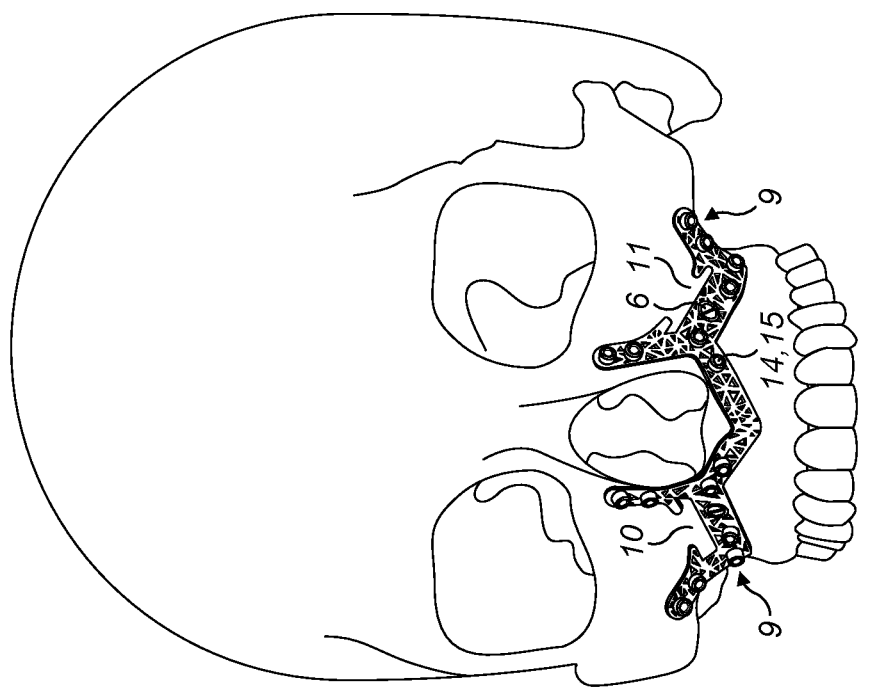

In both the above cases, i.e. in relation to FIG. 12 or FIG. 13, the drilling guide 9 is held in a stable state. In this case, the surgeon then drills the bores (sixteen in number in this example) at the provided locations corresponding to the drilling guiding holes in the guide. For example, FIG. 14 shows at least a portion of a drill bit 8 being inserted into one of the guiding holes of the guide 9 so as to drill a bore.

If the guide 9 has been stabilized by one or more osteotomy screws, the bores generated by these screws may take the place, in an equivalent number, of a respective one or more bores to be provided at the appointed locations, i.e. at the fixing locations or attachment points.

In certain cases, as part of the stage of defining fixing locations an angle of orientation for an axis associated with one or more of the bores may be also defined based on at least one location of one or more anatomical features of the patient. This axis may be offset from the normal, i.e. offset from an axis perpendicular to the surface of the bone portion.

Figure 15:
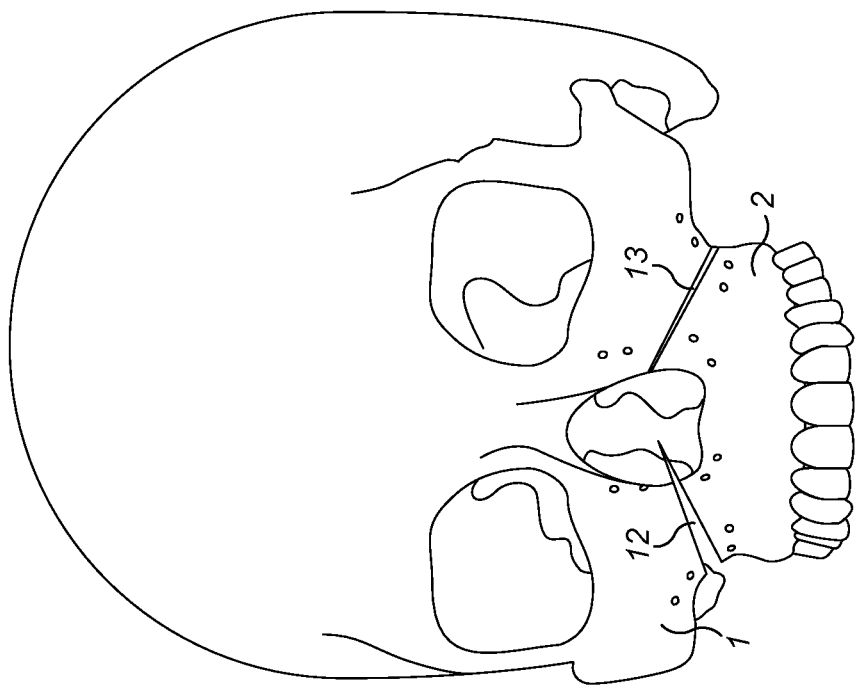

The surgeon can then, in accordance with his preferences, either draw using a pencil or a surgical felt-tip pen the osteotomies delimited by the notches 10 and 11, or immediately use these notches to initiate the osteotomies. This is shown in FIG. 15.

Figure 16:
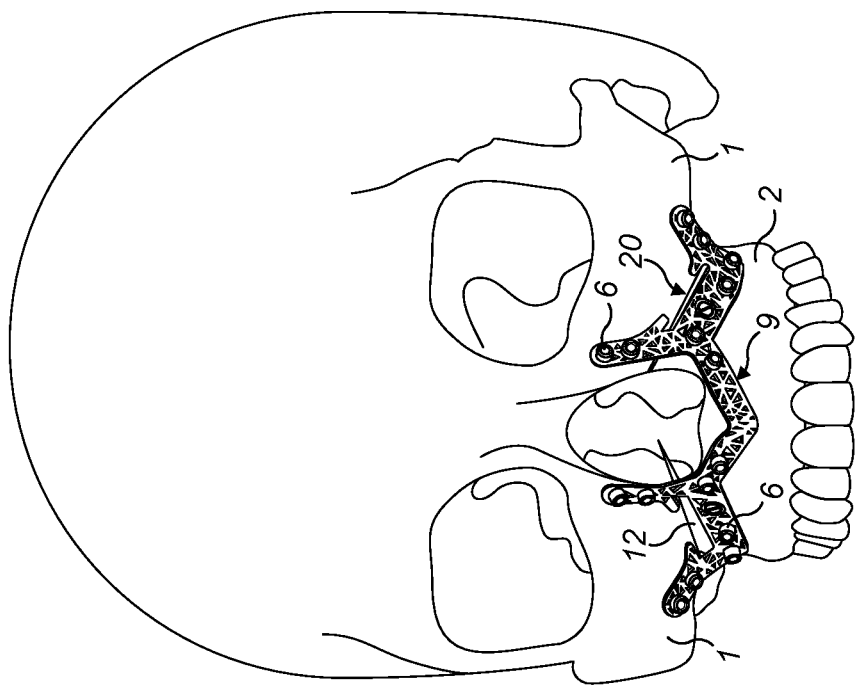

The surgeon then removes the guide, after having removed the temporary stabilization screws, if he had placed any of them. In one case, using a tool 20, for example, a saw, a milling cutter, a laser, etcetera, he finalizes or carries out the osteotomy operation 12, 13 which allows him to release, and therefore move, the maxillary. This is shown in FIG. 16.

Figure 18:
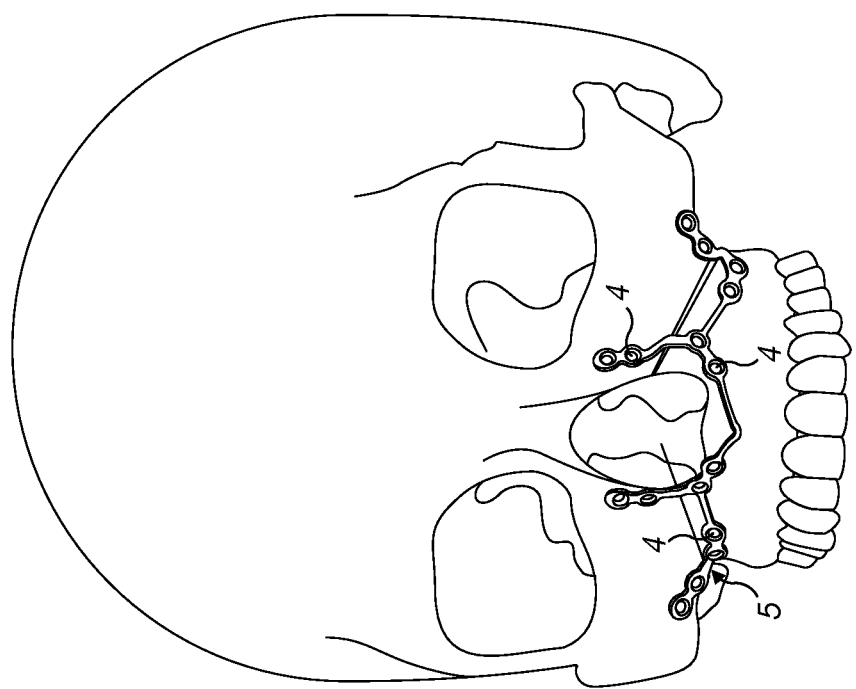
Figure 17:
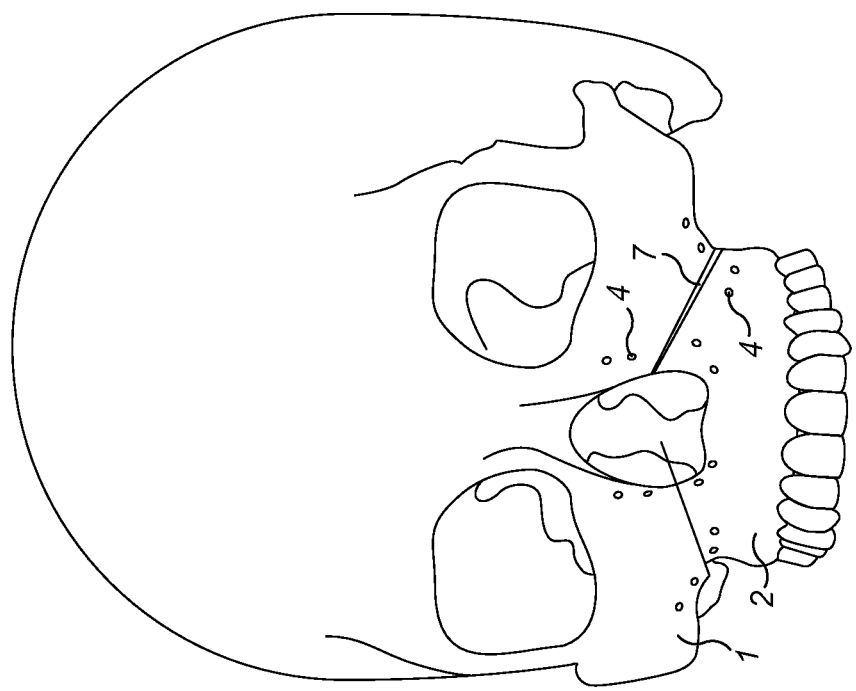

The surgeon can consequently in future freely move the second portion 2 of the bone and bring it into contact with the first portion 1 of the bone, in their desired relative position as is shown in FIG. 17. Due to the customized nature of the structure of the implant 5, the surgeon is only able to fix the two portions 1 and 2 in a single desired position or configuration using the implant 5. For example, it is only in one position or configuration in three-dimensional space that the axes of the apertures for the osteosynthesis screws 6 provided for construction in the implant 5 will correspond to the bores produced in the two bone portions during the operation seen in FIG. 14. This is shown in FIG. 18.

Figure 19:
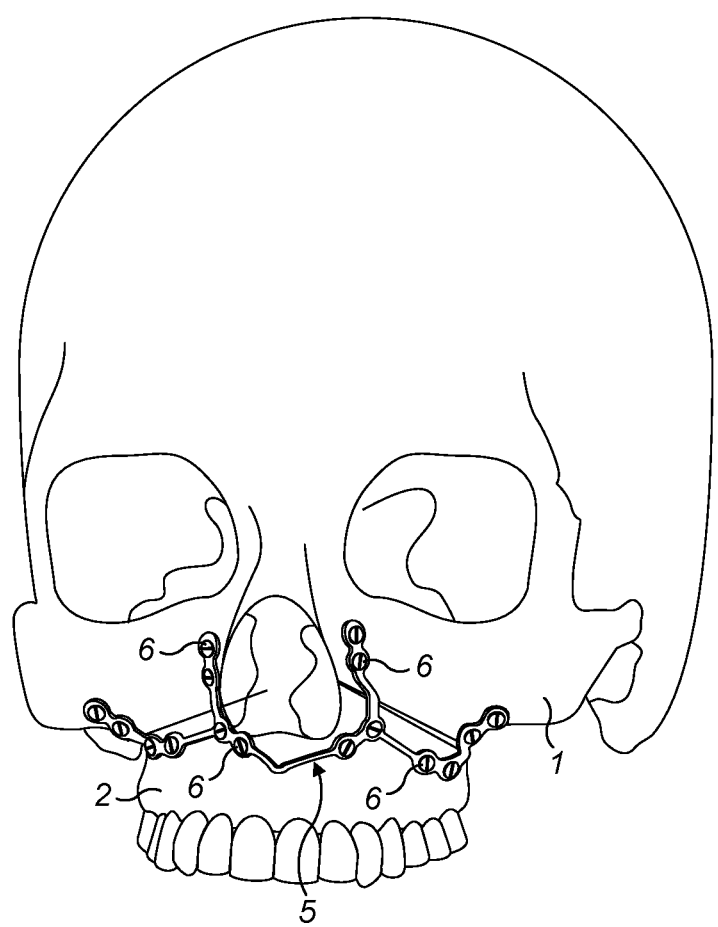

Finally, it is sufficient for the surgeon to definitively fix the two bone portions 1 and 2 using the implant 5 by inserting osteosynthesis screws 6 at their fixing locations 4 and thus screwing them into the sixteen bores produced in the bone portions. This is shown in FIG. 19.

It was set out previously that the precise positions of the bores which are intended to receive the future screws of the implant 5 were indicated on the modified model. Therefore, in one case, the positions of all the bores is produced in a planned manner before the osteotomy is carried out. This in turn means that in surgery the bores and fixing locations are fully defined by the guide 9 and implant 5. This reduces the need for precision during the later surgical operations.

In one particular example, in accordance with a knowledge of the anatomy of the patient, it can be ensured that the bores for the osteotomy screws do not contact any deep-lying major organ. For example, the surgical guide 9 may be defined such that the bores are subsequently guided during drilling to avoid certain anatomical areas.

To this end, as shown in FIGS. 10a and 10b, one or more drill bushes 15 are defined that are either insertable into each of the drilling guiding holes of the guide or form part of guide structure defining the holes. According to this particular example, a drill bush 15 has a height which is predetermined to avoid high-risk anatomical features of the patient. Additionally, or alternatively, a drill bush 15 may be configured such that a subsequently drilled bore 14 has an axis of orientation that also avoids high-risk anatomical features of the patient.

FIG. 10a shows a drill bit 8 that is used to drill a bore 14. The bore 14 then receives an osteotomy screw 6 to fasten the implant 5 and/or guide 9 to the bone portions of the patient as shown in FIG. 10b. In FIG. 10a, the drill bush 15 comprises a stop 16. In use the stop 16 halts the penetration of the drill bit 8 into the bone portions. In more detail, in one example, the stop 16 is formed from a cylindrical upper portion of the drill bush 15, wherein the edge of the upper portion comprises a ledge that extends substantially perpendicular to an axis for the bore 14 and the drill bush 15. This ledge (which in certain examples may comprise a rim, collar or flange) comes into contact with a corresponding collar of the drill bit 8 to prevent further movement of the drill bit 8 along the axis for the bore and the drill bush 15.

In this manner, in addition to or instead of, the precise position of the bores 14, certain exemplary methods ensure that the axis and the depth of the bores is precisely guided. For example, as seen in FIG. 6 the drill bush 15 may form a customized portion of the guide structure, wherein each guiding aperture may comprise a drill bush with a customized height. These drill bushes then form part of the complete manufactured guide structure.

The osteotomy screws 6, one of which is illustrated in FIG. 10b, are therefore at no risk of touching a nerve, a dental root or a vein (i.e. high risk areas of anatomy) when they are screwed into the bone fragments of the patient.

As described herein, the relative spatial arrangement of a plurality of holes for the passage of screws used to secure an implant correspond to the relative spatial arrangement of a plurality of drilling guiding locations. It is possible to configure multiple applications of the described method in the field of facial surgery, for example, in order to repair faults of the mandible, the chin or at least one of the two zygomatic bones.

In this manner, FIGS. 20 to 25 show an application of the method to chin surgery in a second example.

Figure 20:
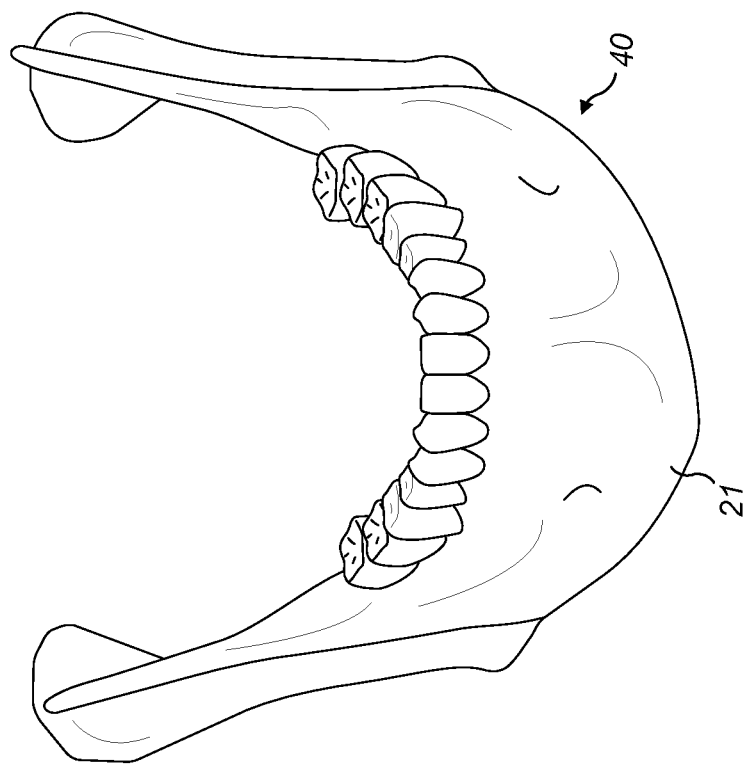

FIG. 20 shows the chin 21 to be repaired.

Figure 21:
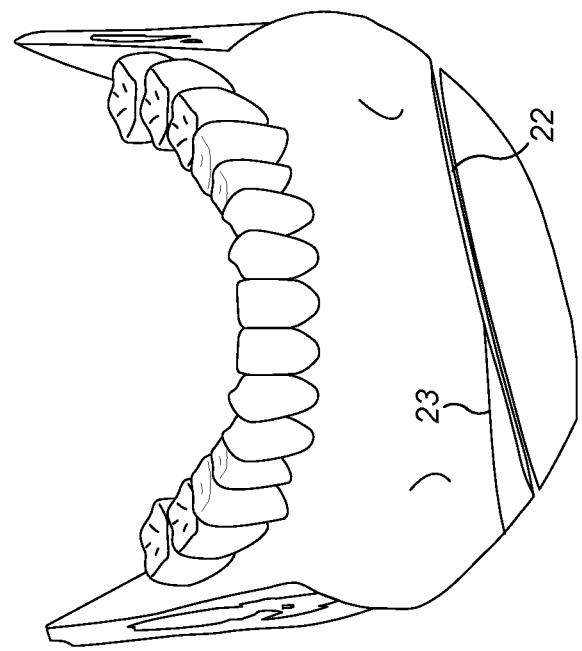
FIGS. 20 to 25 illustrate a second example method applied to chin surgery.

FIG. 21 schematically illustrates along line 22 the osteotomy defined virtually. It further schematically illustrates along line 23 a reference point of a resection which is also desired and defined virtually.

Figure 22:
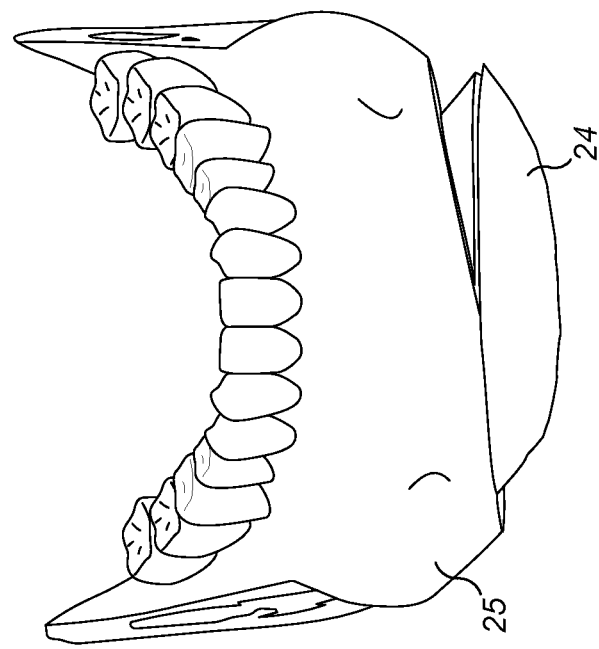

FIG. 22 shows the chin as it should be after the double operation of osteotomy and resection, followed by the repositioning of the second portion 24 of the bone relative to the first portion 25.

Figure 25:
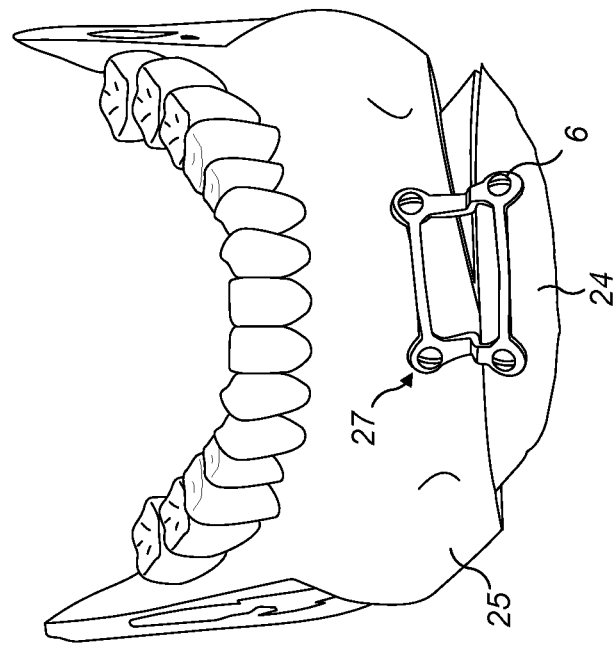

It is known that, on the basis of the final result illustrated in FIG. 25, the following are defined in advance:
  a) the position of the fixing locations 26 of the implant which will fixedly join the portions of bone 24 and 25 in their ideal relative position,
  b) the implant 27, and
  c) the drilling guide 28.

Figure 23:
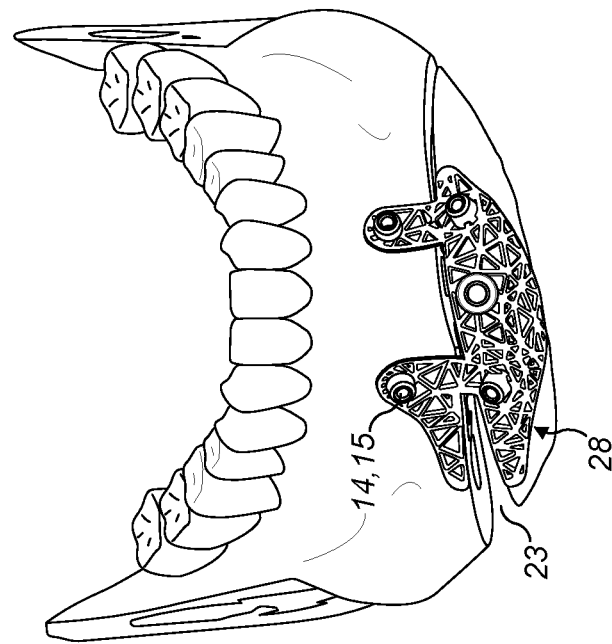

FIG. 23 shows a virtual model of the chin 23 to be repaired. In relation to the chin depicted in the model, in use at a later point, a surgeon may press the drilling guide 28 which is produced in a made-to-measure state. The model of FIG. 23 also shows the result of a resection. In FIG. 23 four drilling guiding holes have been provided in the guide 28. In use, the drilling guide holes guide one or more drill bits to form a plurality of fixing locations 26 which will receive the four fixing screws of the implant 27.

Figure 24:
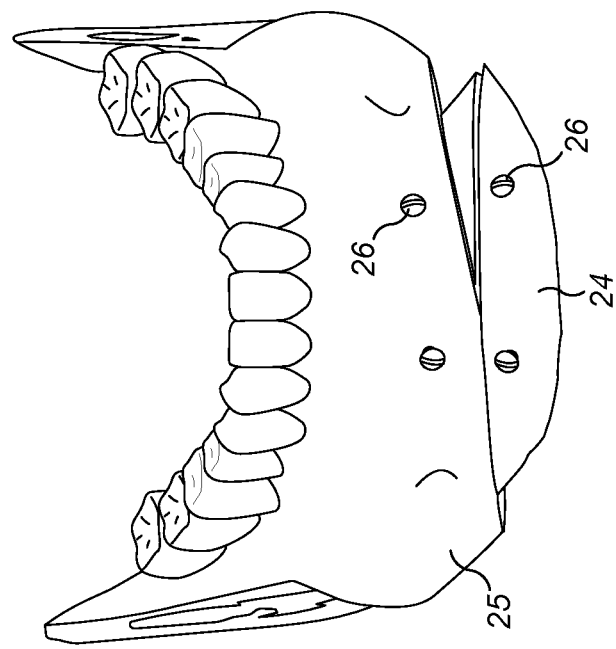

An illustration of four holes 26 drilled in this manner can be seen in FIG. 24 which simultaneously shows the chin as it must be in the ideal final position thereof, that is to say, after the guide 28 has been withdrawn, after osteotomy, after resection and after repositioning of the two bone pieces 24 and 25.

Finally, FIG. 25 illustrates the fixing of the two bone portions of the chin repaired in this manner using the implant 27 which is provided with the four osteosynthesis screws thereof.

By way of a third variant, FIGS. 26 to 31 show an application of the described methods to a mandible reconstruction.

Figure 26:
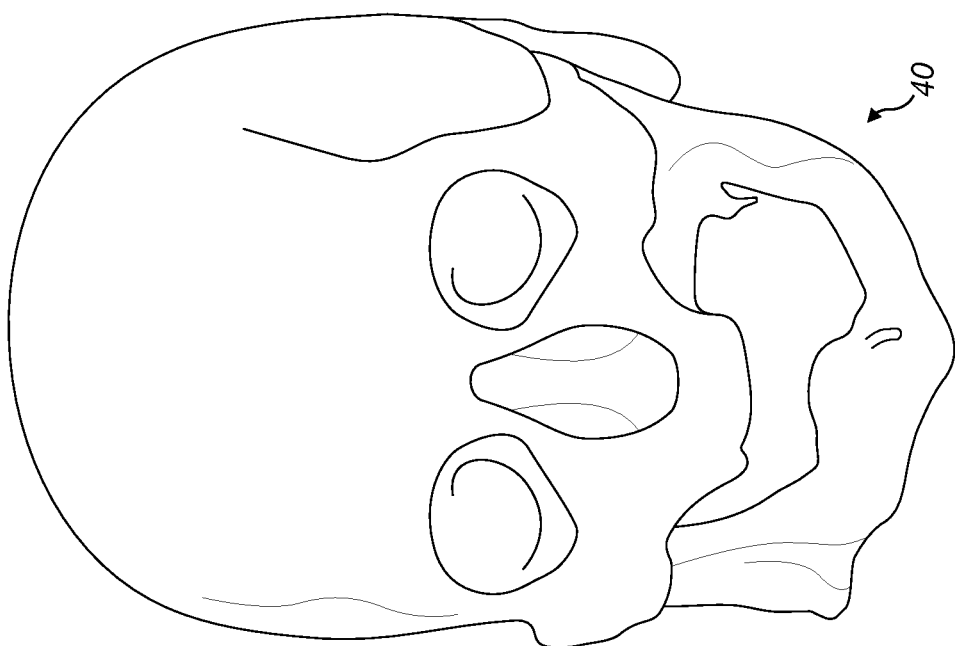
FIGS. 26 to 31 illustrate a third example method applied to the reconstruction of a mandible.
Figure 27:
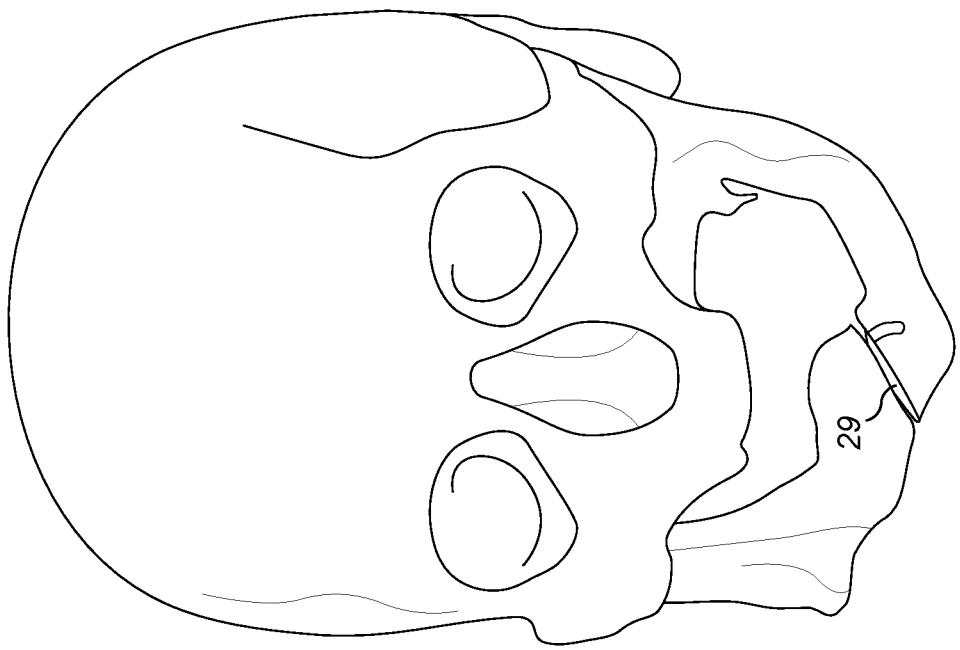

FIG. 26 shows the mandible 40 to be repaired. FIG. 27 shows the cut 29 of the osteotomy defined virtually and FIG. 28 shows, still in a virtual manner, the ideal relative repositioning desired for the two bone portions 30 and 31 which were separated as a result of the virtual osteotomy.

Figure 28:
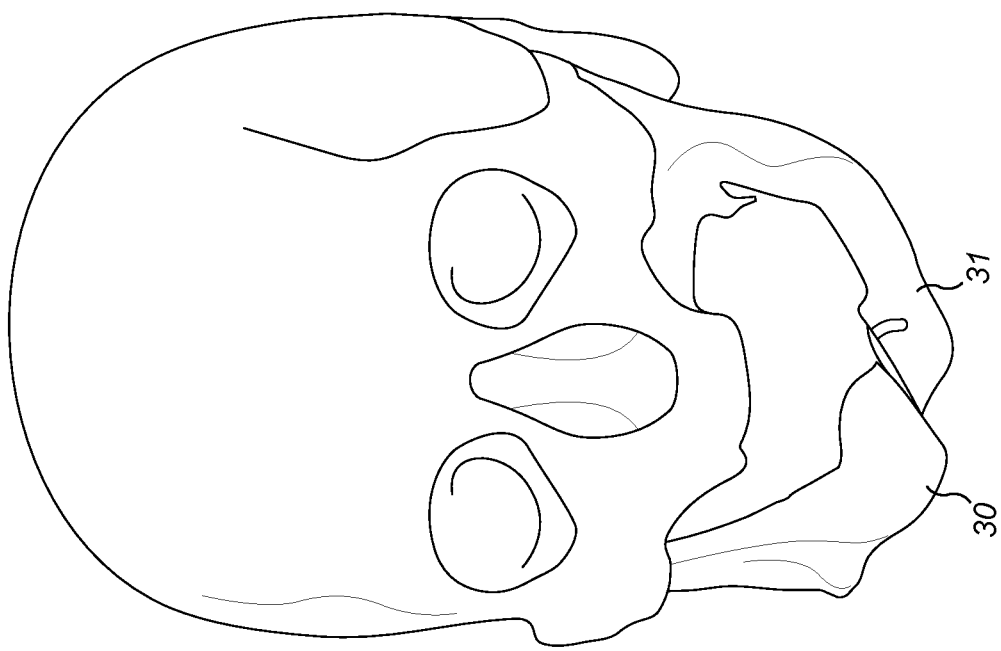

FIG. 28 therefore shows the post-operative shape 50 of the complete bone.

Figure 29:
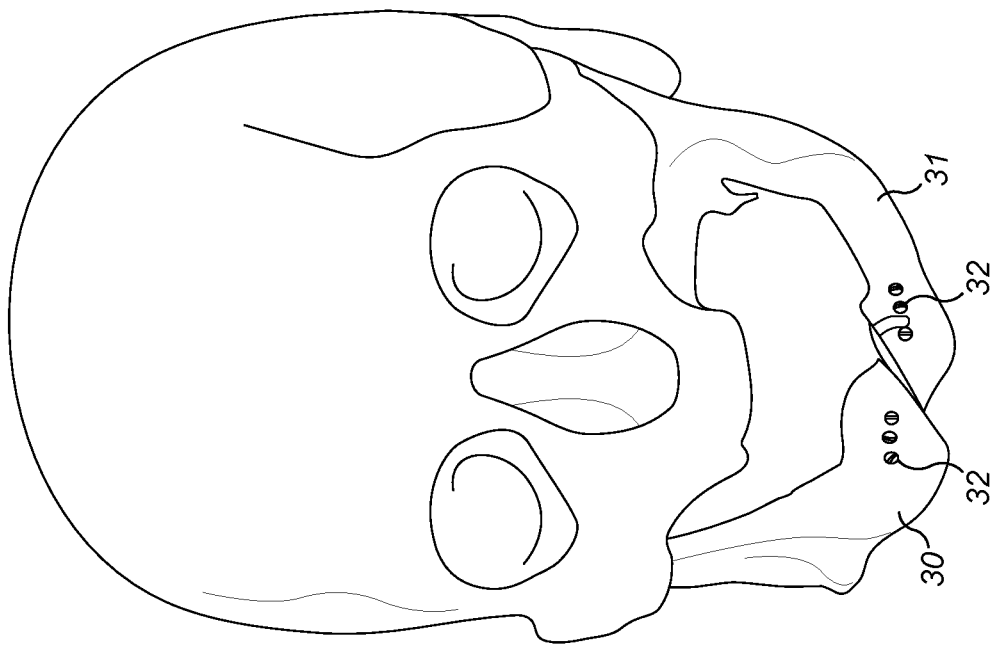

Based on this modified model, therefore, the position of the fixing locations 32 of the future implant 33 are precisely defined as described above. This is shown in FIG. 29. Consequently, by the reverse transformation applied by the computer application and returning to the pre-operative model, the position of the drilling guiding holes of the future drilling guide 34 are defined.

It is seen in FIG. 29 that, in this example, the implant 33 is substantially in the form of an I-shaped plate. There are three fixing locations 32 for osteosynthesis screws, which are aligned with respect to the first portion of the bone 30, and three fixing locations 32, which are aligned with respect to the second portion of the bone 31. In this example, the six fixing locations 32 are themselves arranged substantially in the same alignment.

Having defined the position of the fixing locations or attachment points, and the implant 33 having been drawn, the pre-operative model of FIG. 26 is returned to the drilling guide 34 is determined in such a manner that it will comprise:

six drilling guiding holes 35 which are provided so as to correspond to the six fixing locations 32 after the two bone portions 30 and 31 have been returned to the positions which they occupied before the osteotomy, a notch 36 which is cut in the central portion of the guide 34 in order to act as a reference point, either for drawing the osteotomy line or for initiating the osteotomy.

It is thus simply necessary for the surgeon to place the guide 34 on the mandible of the patient as demonstrated in FIG. 3), to drill in the bone portions 30 and 31 the six fixing locations 32 using for this purpose the six drilling guiding holes 35 of the guide 34, to remove it and to carry out completely or, at the very least, to end the osteotomy operation, following which the mandible of the patient will correspond to that illustrated in FIG. 27, supplemented by six locations 32 which are intended to receive the six fixing screws at the end of the intervention.

Figure 31:
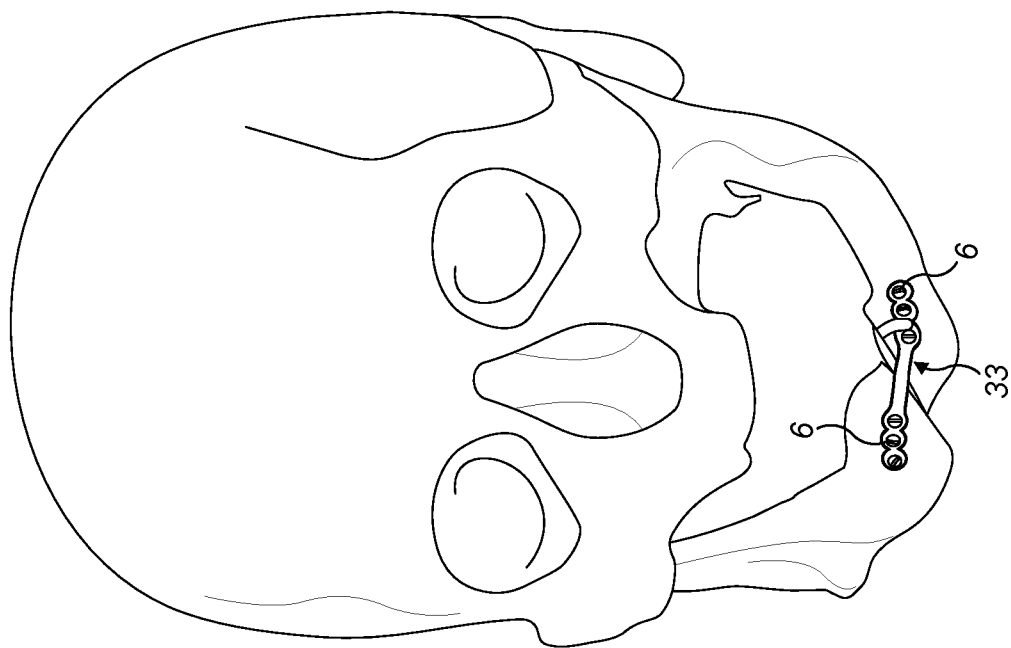
Figure 30:
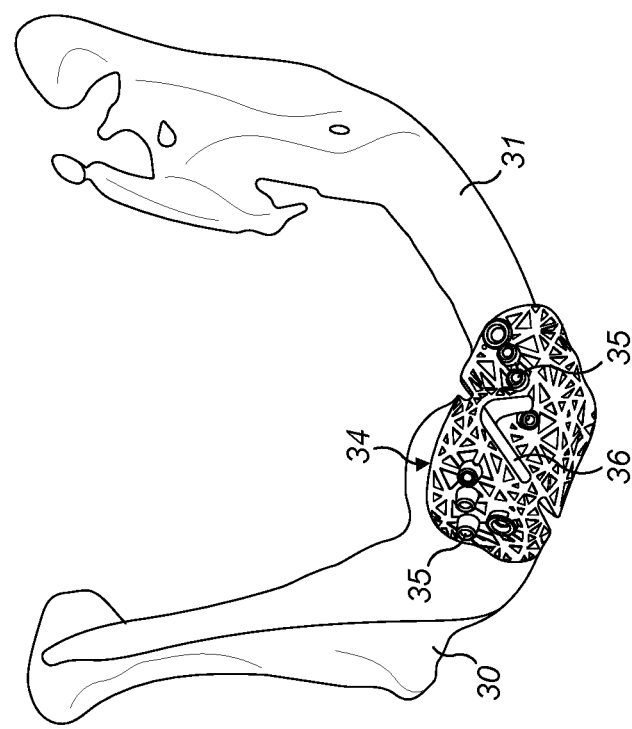

After repositioning the two bone portions in the ideal relative location desired at the outset, a location which is illustrated in FIG. 29, a surgeon then has only to position the implant 33, screwing the six osteosynthesis screws 6 into the six pre-shaped holes 35. FIG. 31 is thus representative of the state of the completed surgical operation.

In one case, for the applications of the method described above by way of examples, each implant and/or each drilling guide is produced from titanium.

Figure 33:
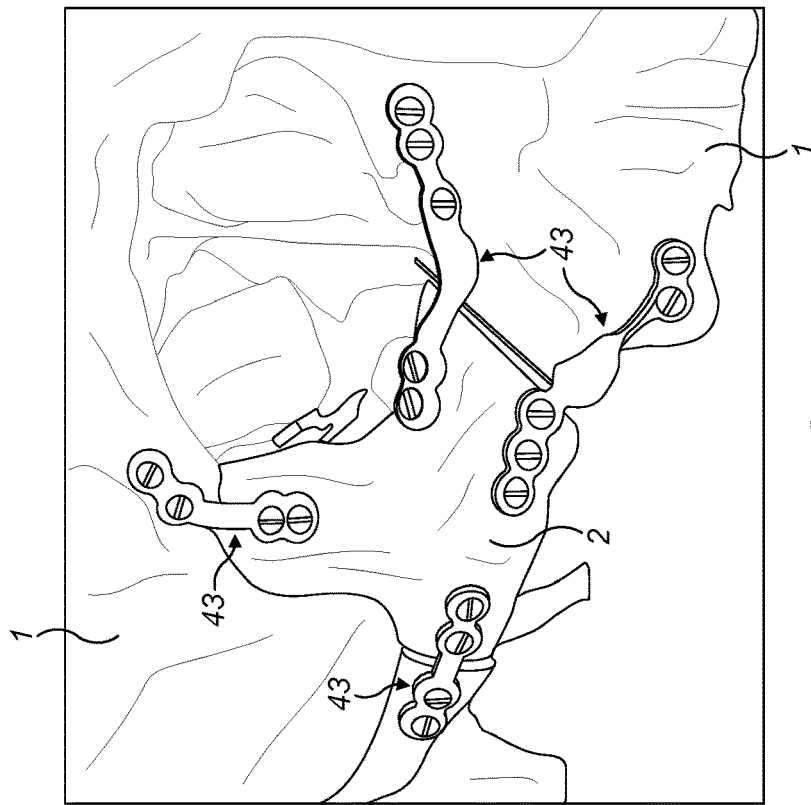
FIGS. 32 and 33 illustrate a fourth example with multiple guides and implants.
Figure 32:

FIG. 32 shows an example wherein the above-described methods are repeated to determine a plurality of monolithic three-dimensional structures for a plurality of surgical guides 44. In the case of FIG. 32 the methods are repeated for a plurality of first bone portions 1 and a common second bone portion 2. In FIG. 33 the above-described methods are repeated to determine a plurality of monolithic three-dimensional structures for a plurality of implants 45. As can be seen, in this example, one structure for a surgical guide corresponds to a plurality of structures for an implant. Such an adaptation may be applied the other way round in other examples, e.g. a plurality of structures for a surgical guide may correspond to one structure for an implant. In FIGS. 32 and 33 the second bone portion 2 is a portion of zygomatic (i.e. cheek) bone; the maxilla may be seen to the right of the Figures with the eye socket in the top left quadrant of the Figures and the nasal cavity towards the top of each Figure.

Figure 34A:
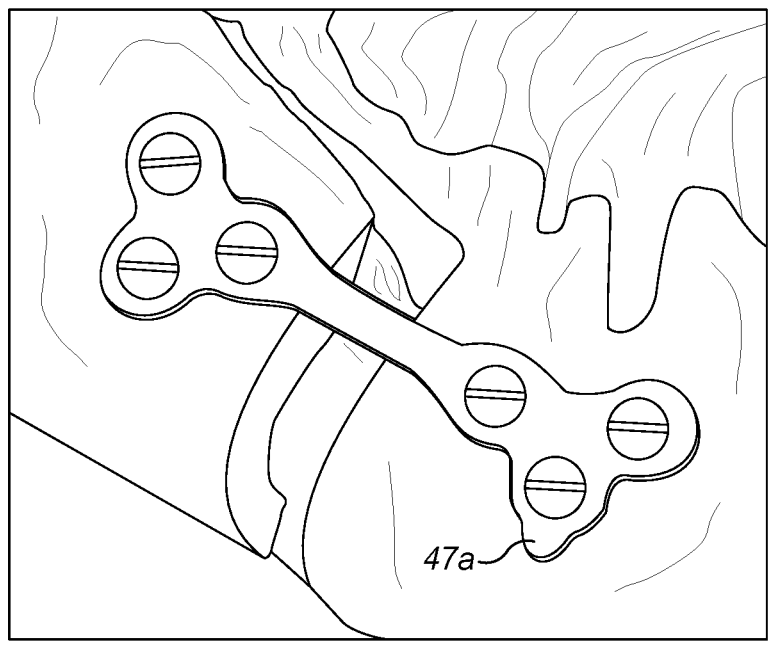
FIGS. 34a and 34b illustrate a variation of the examples.
Figure 34B:
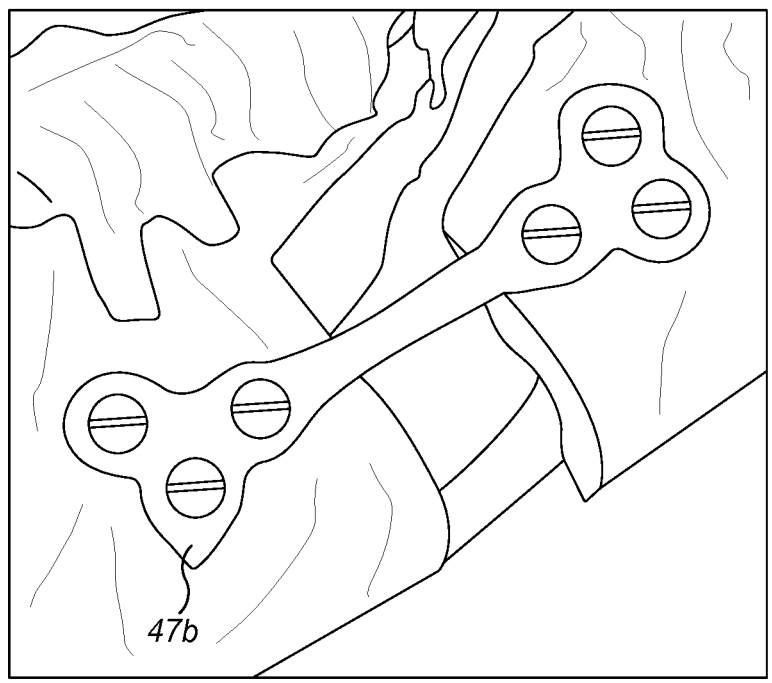

FIGS. 34a and 34b demonstrate how a portion of a first structure for a first implant or first surgical guide may be defined and subsequently manufactured that distinguishes said first structure from a second structure for a second implant or second surgical guide. For example, protrusion 47a in FIG. 34a distinguishes the upper implant, for use on one side of a jaw, from another similar lower implant with a different protrusion 47b shown in FIG. 34b for use on the other side of the jaw.

Figure 35A:
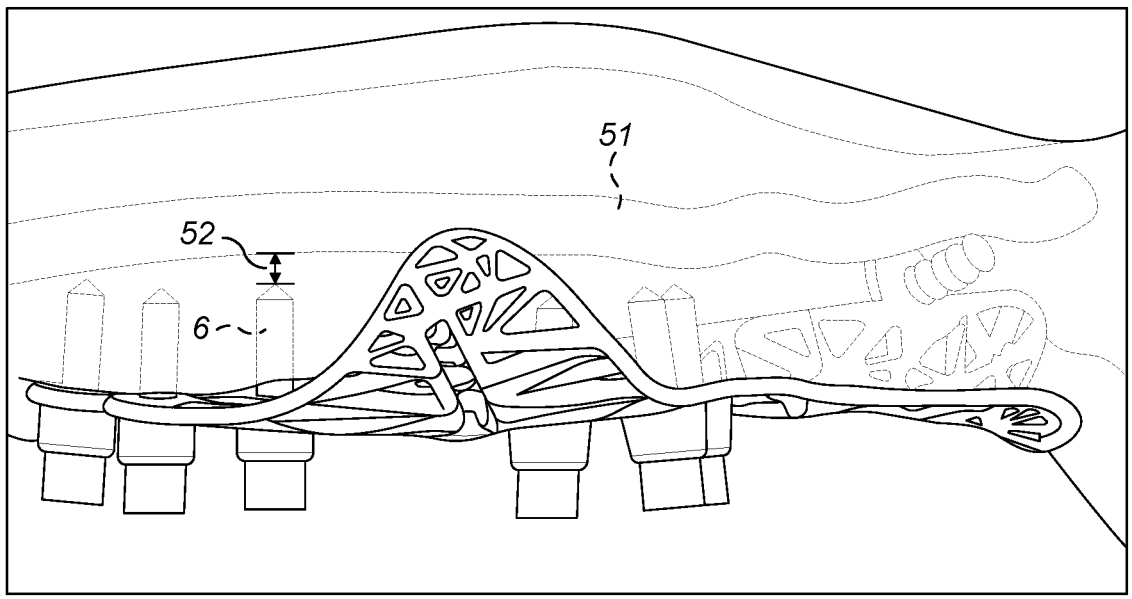
FIGS. 35a and 35b illustrate the avoidance of high-risk anatomical areas.
Figure 35B:
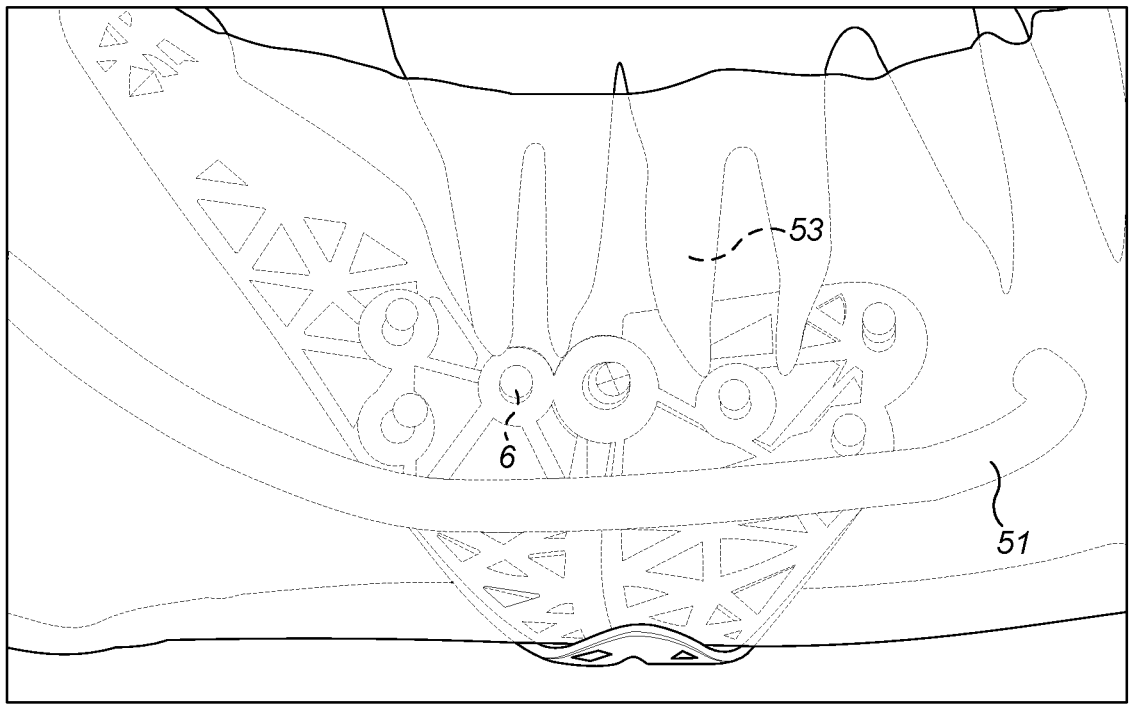

FIGS. 35a and 35b show a nerve 51 and a tooth root 53. It can be seen in FIG. 35a how a proposed bore for a screw 6 is defined to avoid the nerve 51 by distance 52. This may be achieved by defining one or more of the depth and orientation of the bore, which is then used to define the guide structure. Likewise said bores in FIG. 35b, in use filled with the screws 6 of the implant, also avoid the tooth root 53.

In a comparative example, the osteotomy, and/or the resection operation, must be strictly in accordance with that/those which the surgeon has previewed virtually on his computer. This is because, when the surgeon fixes an implant to a portion of the bone which has been separated, he will need to fix the implant to a first portion of the bone using a few screw passage holes which have been provided in a completely arbitrary, non-programmed manner. For example, they may be based on fixing holes which have been pre-drilled in an arbitrary manner. On this occasion it is difficult to correct any imperfection of the osteotomy operation and/or the resection operation. However, according to methods described herein the pre-determined attachment points and the associated bores as guided by the custom drill guide, ensure a precise alignment of bone portions and reduce the effect of any imperfections in the osteotomy.

In an example, there is a method for producing together, in a made-to-measure state, a pre-shaped implant arranged in order, using screws, to fix a first portion of a bone to a second portion of this bone which must be separated from the first portion by an osteotomy operation, and a guide which is also preformed for guiding the drilling of holes for the screws and for guiding the osteotomy. In such a method, there are the steps, before the osteotomy operation, of:

a) using a computer, producing a pre-operative model of the complete bone, in three dimensions, constituting a pre-operative shape of the complete bone, and modifying the pre-operative model, in order to produce a model modified by the fact that it comprises:

a1) a planned post-operative shape of the complete bone, and a2) drilling guiding holes for the screws in the second portion of the bone which must be separated and at least one reference point for the osteotomy template, b) then producing in a made-to-measure state:

b1) a pre-shaped bone fixing implant which is arranged in a pre-operative manner so as to correspond to the planned post-operative shape of the complete bone, the implant comprising a pre-shaped element in order to allow the first portion and the second portion of the bone to be fixed to each other, by producing on the pre-shaped implant, for the second portion of the bone which must be separated, through-holes for the screws corresponding to the drilling guiding holes for the screws of the modified model, by providing in an arbitrary, non-planned manner in the pre-shaped implant holes for the passage of screws which are intended to allow the implant to be fixed to the first portion of the bone, and b2) a pre-shaped drilling guide which is arranged in a pre-operative manner so as to correspond to the pre-operative shape of the complete bone, by producing on this guide, for the second portion of the bone which must be separated, drilling guiding holes for the screws corresponding to the drilling guiding holes for the screws of the modified model.

During the operation for modifying the model seen in step a), there may further comprise:

producing on the modified model, in addition to the drilling guiding holes for the screws provided for the second portion of the bone which must be separated and the osteotomy template reference point(s), additional drilling guiding holes for the screws for the first portion of the bone, 2) during the operation for made-to-measure production seen in step b), producing on the pre-shaped drilling guide additional drilling guiding holes for the screws for the first portion of the bone and ensuring that the holes provided in the implant for the passage of the screws which are intended to allow the implant to be fixed to the first portion of the bone correspond to the additional drilling guiding holes produced in the modified model, the complete relative spatial arrangement of all the passage locations for the screws produced using the drilling guide on the modified model corresponding to the complete relative spatial arrangement of all the holes for the passage of the screws produced on the implant.

In certain examples described herein, specific features of at least one guide and at least one implant are determined and/or produced in a made-to-measure state. In this case a guide is, to some degree, configured to correspond to the initial situation to be corrected and an implant is, to some degree, configured to correspond to the ideal planned situation. In this case, a correspondence is made between the drilling guiding holes for the fixing screws for the first portion of the bone and the through-holes for the screws for the first portion of the bone produced in the implant. This results in the implant, owing to its construction, accurately joining the first portion of the bone with respect to the second portion(s) of the bone, even if the osteotomy, or the resection, is imperfect or approximate.

Consequently, by using a guide and/or implant as described herein a surgeon need not delay carrying out an osteotomy, and optionally a resection operation, due to the need to have the greatest precision. He knows in advance that the implant will ideally join all the portions of bone in the region of the face of the patient he is dealing with since the guiding holes of the fixing screws all have defined positions, both on the first portion of the bone and on the second portion(s) of the bone.

In order to reduce the risk of touching a deep-lying major organ, for example, a nerve, a vein, a dental root, etcetera, methods as described herein make provision, in addition to the precise position of each bore which is intended to receive a fixing screw, for the drilling axis and/or the depth thereof also to be determined in a precise manner.

In this manner, a drilling guide as described in examples herein comprises, with respect to at least one of the drilling guiding holes with which it is provided, a drill bush whose axis will correspond to the drilling axis and whose height will be such that it will secure the drilling by limiting the depth thereof in order to eliminate any risk of bringing the drill bit into contact with a major organ.

Certain methods described herein make provision for the second portion of the bone which must be separated from the first portion by an osteotomy operation to be able to be separated itself into several fractions.

Examples described herein also relate to a pre-shaped implant which is obtained by carrying out certain methods described above. This implant is intended to fix, using screws, a first portion of a bone to a second portion of this bone which must be separated from the first portion by an osteotomy operation. The implant is produced in a made-to-measure state so as to correspond to the modified model which constitutes the planned post-operative shape of the complete bone. This implant comprises, for the second portion of the bone which must be separated, through-holes for the screws which correspond to the drilling guiding holes for the screws of the modified model. The implant is determined such that it further comprises, for the first portion of the bone, holes for the passage of the screws, which holes correspond to the drilling guiding holes produced in the modified model for the screws which are intended for the first portion of the bone.

The implant described in the example above therefore has, with respect to the first portion of the bone, holes for the passage of fixing screws that are planned and correspond to the drilling guiding holes produced in the modified model for the screws which are intended for this same first portion of the bone.

In other words, the complete relative spatial arrangement of some or all of the holes for the passage of the fixing screws produced in the implant corresponds to the complete relative spatial arrangement of some or all of the drilling guiding holes for the screws, produced in the modified model. The implant can therefore occupy only one position on the face of the patient, after the osteotomy operation and after any resection operation. It is therefore of no consequence that the osteotomy and/or the resection is/are imperfect or approximate.

An important factor is that, after fixing the implant using the osteosynthesis screws, the second portion of the bone or the second portions of the bone is excellently positioned relative to the first portion of the bone. Thus, after the bone reconstruction and the joining of all of the operated zone, the first and second portions of the bone of the patient will be joined as originally desired.

In the same context, examples described herein relate to a pre-shaped drilling guide which is obtained by carrying out the method described above and which is intended to guide the osteotomy and/or guide the drilling of holes for the screws which are used to fix, using the implant which has also been described above, a first portion of a bone to a second portion of this bone. The guide is produced in a made-to-measure state and comprising, for the second portion of the bone which must be separated, drilling guiding holes for the screws corresponding to the drilling guiding holes for the screws of the modified model, the drilling guide being configured such that it further comprises, for the first portion of the bone, drilling guiding holes for the screws, which holes correspond to the drilling guiding holes produced in the modified model for the screws which are intended for the first portion of the bone.

In certain examples, in contrast to comparative drilling guides, a drilling guide extends from both sides of a line along which the osteotomy is due to be carried out. By projecting beyond this line, numerous holes may be provided for guiding the drilling of the screws which are intended to be fixed in the first portion of the bone.

Furthermore, the position of these holes is predetermined in terms of production so as to correspond to the holes that are defined in the modified model with respect to the first portion of the bone.

A consequence of this construction is that, after all the planned holes have been drilled, using the guide, in the first and second portions of the bone, after the osteotomy has been supplemented by the optional resection, and finally after the planned repositioning of the bone portions, in accordance with what was envisaged at the outset, the complete relative spatial arrangement of some or all of the passage locations for the screws produced using the drilling guide is such that, in the repositioned portions of the bone, it corresponds precisely to the complete relative spatial arrangement of some or all the holes for the passage of the screws produced in the implant.

That is to say, the drilling guide in with certain examples described herein ensures that some or all of the holes drilled before the osteotomy in the first and second portions of the bone, after the osteotomy and the ideal repositioning of the portions of the bone carried out by the surgeon, are in alignment with the holes which have been drilled in the pre-shaped implant.

Finally, examples relate to a kit or assembly which is constituted by an implant and a drilling guide which are produced together in a made-to-measure state. In this case the complete relative spatial arrangement of some or all of the passage locations for the screws produced using the drilling guide, on the modified model, correspond to the complete relative spatial arrangement of some or all of the holes for the passage of the screws produced in the implant. For example, locations of the first and second plurality of apertures in the maxillofacial surgical guide correspond to mapped locations of the first and second plurality of apertures in the maxillofacial implant, wherein the locations of the first and second plurality of apertures in the maxillofacial surgical guide correspond to a pre-operative maxillofacial anatomy, and wherein the locations of the first and second plurality of apertures in the maxillofacial implant correspond to a desired post-operative maxillofacial anatomy.

The examples described above are not limiting, variation and combination of any of the examples may occur. The examples cover all possible production variants, as long as they do not depart from the scope delimited by the appended claims which define the present invention.

What is claimed is:

1. A method for configuring a surgical guide and an associated implant for maxillofacial osteosynthesis, the method comprising:
    accessing data indicative of a pre-operative maxillofacial anatomy of a patient and generating a three-dimensional model of said anatomy using said data;
    generating a modified three-dimensional model indicative of a desired post-operative orientation of first and second bone portions based on an arrangement of the second bone portion in relation to the first bone portion, said arrangement comprising at least one of a translation and a rotation of the second bone portion in relation to the first bone portion, the first and second bone portions having been defined by a simulated osteotomy on the three-dimensional model of the pre-operative maxillofacial anatomy, said simulated osteotomy defining at least one cut that results in the second bone portion being separated from the first bone portion, said osteotomy resulting in an absence of any bone coupling the first and second bone portions together;
    determining a monolithic three-dimensional structure for the implant that couples first and second pluralities of attachment points in the modified three-dimensional model, wherein on the modified three-dimensional model the first plurality of attachment points have been defined on the first bone portion and the second plurality of attachment points have been defined on the second bone portion, and wherein the monolithic three-dimensional structure for the implant has a shape that varies in each of three dimensions to arrange the second bone portion relative to the first bone portion in accordance with the desired post-operative orientation, each of at least one of the attachment points corresponding to an aperture for a bone fixation device in said structure for the implant;
    mapping the first and second plurality of attachment points to corresponding locations on the three-dimensional model of the pre-operative maxillofacial anatomy; and
    determining a monolithic three-dimensional structure for the surgical guide that couples the corresponding locations in the three-dimensional model of the pre-operative maxillofacial anatomy, wherein each of at least one of the corresponding locations corresponds to a guide aperture in said structure for the surgical guide.

2. The method according to claim 1,
    wherein the three-dimensional structure for the surgical guide defines an inner surface that varies in each of three dimensions,
    wherein the inner surface has a shape that aligns with an outer surface defined by the first bone portion and the second bone portion in a pre-operative state,
    wherein the three-dimensional structure for the surgical guide is configured such that the inner surface aligns with the outer surface at a single position in three-dimensional space.

3. The method according to claim 1,
    wherein the three-dimensional structure for the implant has a first portion that has an inner surface that matches an outer surface as defined by an anatomy of the first bone portion, and
    wherein the three-dimensional structure for the implant has a second portion that has an inner surface that matches an outer surface as defined by an anatomy of the second bone portion.

4. The method according to claim 1, comprising:
    for at least one selected guide aperture in the monolithic three-dimensional structure for the surgical guide, defining a drill bush,
    wherein said defining comprises determining a height for the drill bush based on at least one location of one or more anatomical features of the patient.

5. The method according to claim 1, wherein the monolithic three-dimensional structure for the surgical guide comprises one or more cutting guides that correspond with one or more of the at least one cut defined by the simulated osteotomy.

6. The method according to claim 5, wherein one or more of the one or more cutting guides is elongate.

7. The method according to claim 1, comprising:
for a selected attachment point, defining an angle of orientation for an axis associated with a bore based on at least one location of one or more anatomical features of the patient.

8. The method according to claim 7, wherein the axis is offset from a normal to a surface of one of the first and second bone portions.

9. The method according to claim 1, wherein the second bone portion comprises a plurality of bone portions that result from a plurality of cuts.

10. The method according to claim 1,
wherein the method is repeated to determine a plurality of monolithic three-dimensional structures for one or more of a plurality of implants and a plurality of surgical guides,
wherein the method is repeated for a plurality of first bone portions and a common second bone portion.

11. The method according to claim 10, comprising:
defining a portion of a first structure for a first implant or first surgical guide that distinguishes said first structure from a second structure for a second implant or second surgical guide.

12. A method according to claim 10,
wherein one structure for a surgical guide corresponds to a plurality of structures for an implant, or
a plurality of structures for a surgical guide corresponds to one structure for an implant.

13. The method according to claim 1, the first and second bone portions having been defined by a simulated resection on the three-dimensional model of the pre-operative maxillofacial anatomy, said simulated resection defining at least one further cut that results in a third bone portion being separated from the first and second bone portions.

14. The method according to claim 13, wherein the simulated resection is based on a determined interference between the first and second bone portions in the arrangement of the second bone portion in relation to the first bone portion.

15. The method according to claim 13, wherein the monolithic three-dimensional structure for the surgical guide comprises one or more further cutting guides that correspond with one or more of the at least one further cut.

16. The method according to claim 15, wherein one or more of the one or more further cutting guides is elongate.

17. A method for configuring a surgical guide and an associated implant for maxillofacial osteosynthesis, the method comprising:
accessing data indicative of a pre-operative maxillofacial anatomy of a patient and generating a three-dimensional model of said anatomy using said data;
generating a modified three-dimensional model indicative of a desired post-operative orientation of first and second bone portions based on an arrangement of the second bone portion in relation to the first bone portion, said arrangement comprising at least one of a translation and a rotation of the second bone portion in relation to the first bone portion, the first and second bone portions having been defined by a simulated osteotomy on the three-dimensional model of the pre-operative maxillofacial anatomy, said simulated osteotomy defining at least one cut that results in the second bone portion being separated from the first bone portion, said osteotomy resulting in an absence of any bone coupling the first and second bone portions together;
determining a monolithic three-dimensional structure for the implant that couples first and second pluralities of attachment points in the modified three-dimensional model, wherein on the modified three-dimensional model the first plurality of attachment points have been defined on the first bone portion and the second plurality of attachment points have been defined on the second bone portion, and wherein the monolithic three-dimensional structure for the implant has a shape that varies in each of three dimensions to arrange the second bone portion relative to the first bone portion in accordance with the desired post-operative orientation, each of at least one of the attachment points corresponding to an aperture for a bone fixation device in said structure for the implant;
mapping the first and second plurality of attachment points to corresponding locations on the three-dimensional model of the pre-operative maxillofacial anatomy;
determining a monolithic three-dimensional structure for the surgical guide that couples the corresponding locations in the three-dimensional model of the pre-operative maxillofacial anatomy, wherein each of at least one of the corresponding locations corresponds to a guide aperture in said structure for the surgical guide; and
manufacturing the implant based on the determined monolithic three-dimensional structure for the implant.

18. The method according to claim 17, wherein said manufacturing comprises additive manufacturing based on data defining a three-dimensional structure.

19. A method for configuring a surgical guide and an associated implant for maxillofacial osteosynthesis, the method comprising:
accessing data indicative of a pre-operative maxillofacial anatomy of a patient and generating a three-dimensional model of said anatomy using said data;
generating a modified three-dimensional model indicative of a desired post-operative orientation of first and second bone portions based on an arrangement of the second bone portion in relation to the first bone portion, said arrangement comprising at least one of a translation and a rotation of the second bone portion in relation to the first bone portion, the first and second bone portions having been defined by a simulated osteotomy on the three-dimensional model of the pre-operative maxillofacial anatomy, said simulated osteotomy defining at least one cut that results in the second bone portion being separated from the first bone portion, said osteotomy resulting in an absence of any bone coupling the first and second bone portions together;
determining a monolithic three-dimensional structure for the implant that couples first and second pluralities of attachment points in the modified three-dimensional model, wherein on the modified three-dimensional model the first plurality of attachment points have been defined on the first bone portion and the second plurality of attachment points have been defined on the second bone portion, and wherein the monolithic three-dimensional structure for the implant has a shape that varies in each of three dimensions to arrange the second bone portion relative to the first bone portion in accordance with the desired post-operative orientation, each of at least one of the attachment points corresponding to an aperture for a bone fixation device in said structure for the implant;

mapping the first and second plurality of attachment points to corresponding locations on the three-dimensional model of the pre-operative maxillofacial anatomy;

determining a monolithic three-dimensional structure for the surgical guide that couples the corresponding locations in the three-dimensional model of the pre-operative maxillofacial anatomy, wherein each of at least one of the corresponding locations corresponds to a guide aperture in said structure for the surgical guide; and manufacturing the surgical guide based on the determined monolithic three-dimensional structure for the surgical guide.

20. The method according to claim 19, wherein said manufacturing comprises additive manufacturing based on data defining a three-dimensional structure.

* * * * *